United States Patent [19]

Ondetti et al.

[11] 4,154,840

[45] May 15, 1979

[54] ANTIHYPERTENSIVE PIPECOLIC ACID DERIVATIVES

[75] Inventors: Miguel A. Ondetti, Princeton; David W. Cushman, West Windsor, both of N.J.

[73] Assignee: E. R. Squibb & Sons, Inc., Princeton, N.J.

[21] Appl. No.: 884,791

[22] Filed: Mar. 9, 1978

Related U.S. Application Data

[60] Division of Ser. No. 751,851, Dec. 22, 1976, Pat. No. 4,105,776, which is a continuation-in-part of Ser. No. 698,432, Jun. 21, 1976, abandoned, which is a continuation-in-part of Ser. No. 657,792, Feb. 13, 1976, Pat. No. 4,046,889.

[51] Int. Cl.² .................. A61K 31/445; C07D 211/60
[52] U.S. Cl. .................. 424/267; 546/188; 546/189; 546/221; 546/226; 546/242; 546/245
[58] Field of Search .................. 260/293.63, 293.73, 260/293.85; 424/267

[56] References Cited

U.S. PATENT DOCUMENTS 4,091,024  5/1978  Ondetti et al. .................. 260/293.85

OTHER PUBLICATIONS

Chemical Abstracts, 41:3208g (1947) [Thomson, J., et al., J. Pharmacol., 89, 1–13 (1947)].

*Primary Examiner*—Natalie Trousof
*Assistant Examiner*—Richard A. Schwartz
*Attorney, Agent, or Firm*—Lawrence S. Levinson; Merle J. Smith

[57] ABSTRACT

New proline derivatives and related compounds which have the general formula

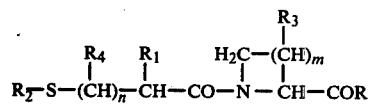

are useful as angiotensin converting enzyme inhibitors.

36 Claims, No Drawings

ANTIHYPERTENSIVE PIPECOLIC ACID DERIVATIVES

This application is a division of our application Ser. No. 751,851, filed Dec. 22, 1976, now U.S. Pat. No. 4,105,776, issued Aug. 8, 1978, which is a continuation-in-part of our application Ser. No. 698,432, filed June 21, 1976, now abandoned, which is a continuation-in-part of our application Ser. No. 657,792, filed Feb. 13, 1976, now U.S. Pat. No. 4,046,889, issued Sept. 6, 1977.

SUMMARY OF THE INVENTION

This invention relates to new proline derivatives and related compounds which have the general formula

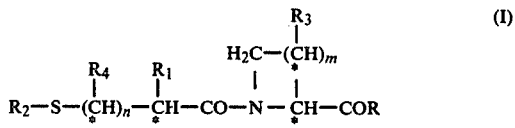

wherein R is hydroxy, $NH_2$ or lower alkoxy;
$R_1$ and $R_4$ each is hydrogen, lower alkyl, phenyl or phenyl-lower alkyl;
$R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, pheny-lower alkylthiomethyl, lower alkanoylamidomethyl,

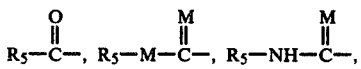

$R_6$—S— or $R_7$;
$R_3$ is hydrogen, hydroxy or lower alkyl;
$R_5$ is lower alkyl, phenyl or phenyl-lower alkyl;
$R_6$ is lower alkyl, phenyl, substituted phenyl, (wherein the phenyl substituent is halo, lower alkyl or lower alkoxy), hydroxy-lower alkyl or amino(-carboxy)-lower alkyl;

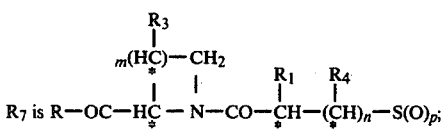

M is O or S;
m is 1 to 3;
n and p each is 0 to 2, and to processes for making them.

The asterisks indicate asymmetric carbon atoms. Each of the carbons bearing a substituent $R_1$, $R_3$ and $R_4$ is asymmetric when that substituent is other than hydrogen.

DETAILED DESCRIPTION OF THE INVENTION

The invention in its broad aspects includes proline and related derivatives having formula I above. Within this broad group, because of their properties, certain subgroups are preferred over others.

Broadly preferred are those compounds of formula I wherein R is hydroxy or lower alkoxy; $R_1$ is hydrogen or lower alkyl; $R_2$ is hydrogen, $R_5$—CO, $R_6$—S—, or $R_7$; $R_3$ and $R_4$ each is hydrogen; $R_5$ is lower alkyl, especially methyl or phenyl; $R_6$ is lower alkyl, especially methyl or ethyl; m is 2, n is 0, 1 or 2, especially 1; and $R_7$ wherein R, $R_1$, $R_3$, $R_4$, m and n have the same preferences as above and p is 0.

Especially preferred are those compounds which have the formula

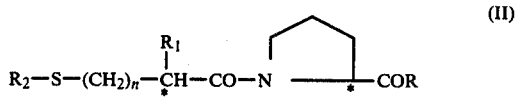

wherein R is hydroxy or lower alkoxy;
$R_1$ is hydrogen or lower alkyl;
$R_2$ is hydrogen, $R_5$—CO—, $R_6$—S— or $R_7$;
$R_5$ is lower alkyl or phenyl, especially the first;
$R_6$ is lower alkyl;
and n is 0, 1 or 2.

Within the group of compounds represented by formula II, the following are still more preferred subgroups in the order (a to r) of increasing preference to the compounds which are especially preferred embodiments:

(a) R is hydroxy
(b) n is 1
(c) $R_2$ is hydrogen or lower alkanoyl
(d) $R_2$ is hydrogen
(e) $R_2$ is acetyl
(f) $R_1$ is hydrogen or lower alkyl
(g) $R_1$ is hydrogen or methyl
(h) R is hydroxy, $R_1$ is hydrogen or methyl
(i) R is hydroxy, $R_1$ is hydrogen or methyl, $R_2$ is hydrogen or acetyl and n is 0, 1 or 2
(j) R is hydroxy, $R_1$ and $R_2$ each is hydrogen and n is 0
(k) R is hydroxy, $R_1$ is hydrogen, $R_2$ is acetyl and n is 1
(l) R is hydroxy, $R_1$ is methyl, $R_2$ is acetyl and n is 1
(m) R is hydroxy, $R_1$ and $R_2$ each is hydrogen and n is 1
(n) R is hydroxy, $R_1$ is methyl, $R_2$ is hydrogen and n is 1
(o) R is hydroxy, $R_1$ is hydrogen, $R_2$ is lower alkylthio and n is 1
(p) $R_2$ is

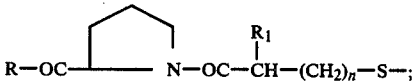

each R is hydroxy; $R_1$ is hydrogen or lower alkyl, especially hydrogen or methyl; and n is 0 to 2, especially 1.

(q) $R_2$ is

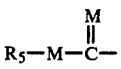

wherein M is O or S
(r) $R_2$ is

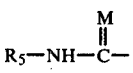

wherein M is O or S, preferably S.

It will be appreciated that combinations of the foregoing, where applicable, are among the preferred groups.

The stereoisomers in which the proline is in the L-form are especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkoxy groups are of the same kind having 1 to 7 carbons linked to oxygen, for example, methoxy, ethoxy, propoxy, isopropoxy, butoxy, isobutoxy, t-butoxy and the like. The $C_1$–$C_4$ members, especially $C_1$ and $C_2$ members, of both types are preferred. Phenylmethyl is the preferred phenyl-lower alkyl group.

The lower alkanoyl groups are those having the acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

The four common halogens are included by the term "halo" but chlorine and bromine are preferred. The substituted phenyl groups preferably bear the substituent in the 4-position of the ring. The hydroxy-lower alkyl groups have a hydroxy group on an alkyl chain like those described above, preferably on the terminal carbon, e.g., hydroxymethyl, 2-hydroxyethyl, etc. The amino(carboxy)lower alkyl groups have one amino and one carboxy on a lower alkyl group such as those described above, preferably both on one carbon, e.g., on the terminal carbon as in the preferred 2-amino-2-carboxyethyl group.

The products of formula I and the preferred subgroups can be produced by various methods of synthesis.

In general, the products of this invention are produced by acylating a compound of the formula

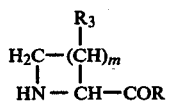   (III)

with an acid of the formula

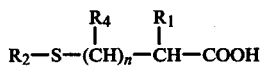   (IV)

or its chemical equivalent.

Thus, the final product can be produced not only by direct acylation with an acid of formula IV but also by intermediates such as (a) ω-haloalkanoic acids of the formula

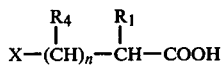   (V)

wherein X is bromo, chloro or iodo, or (b) a tosyloxyalkanoic acid, i.e., X in formula V is tosyloxy

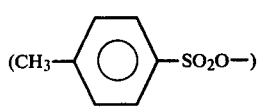

or (c) a substituted acrylic acid of the formula

   (VI)

The product of this acylation is then subjected to displacement or addition with the anion of a thiol or thioacid of the formula (VII) $R_2$—SH Acylation can also be effected with a thiolactone of the formula

   (VIII)

wherein n is 1 or 2, or a mercaptoalkanoic acid of the formula

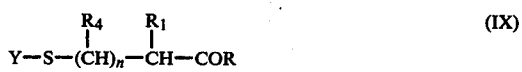   (IX)

wherein Y is $R_2$ or, in addition, if a product of formula I wherein $R_2$ is hydrogen is desired, then Y can also be a protecting group such as

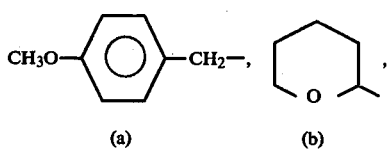

(a)        (b)

(c) $CH_3CONHCH_2$,

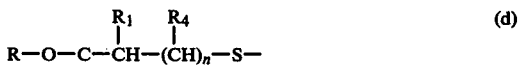   (d)

or other sulfur protecting group. "Deprotection" can be effected by conventional means such as treatment with hot trifluoroacetic acid, cold trifluoromethanesulfonic acid, mercuric acetate, sodium in liquid ammonia, zinc and hydrochloric acid or the like. For a review of these methods see Methoden der Organischen Chemie (Houben-Weyl), Vol. XV, part I, page 736 et seq. (1974).

When the acid of formula IV is used as the acylating agent, the acylation can be effected in the presence of a coupling agent like dicyclohexycarbodiimide or the like, or the acid can be activated by formation of its mixed anhydride, symmetrical anhydride, acid chloride, acid ester or use of Woodward reagent K, N-ethoxycarbonyl-2-ethoxy-1,2-dihydroquinoline or the like. For a review of the methods for acylation, see Methoden der Organischen Chemie (Houben-Weyl), Vol. XV, part II, page 1 et seq. (1974).

Compounds of formula III include, for example, proline, hydroxyproline, 4-methylproline, pipecolic acid, 5-hydroxypipecolic acid, azetidine-2-carboxylic acid, their lower alkyl esters and the like. The acylation of such compounds is described in greater detail below.

According to a preferred method for producing compounds of formula I, especially wherein $R_2$ is $R_5$—

CO—, an acid or ester of formula III is coupled with a haloalkanoic acid of the formula

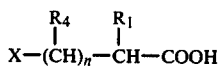 (V)

wherein X is a halogen, preferably chlorine or bromine. This can be effected by one of the known procedures in which the acid IV is activated, prior to reaction with the acid III, involving formation of a mixed anhydride, symmetrical anhydride, acid chloride, active ester, or use of Woodward regent K, EEDQ (N-ethoxycarbonyl-2-ethoxy-1,2-dihydroquinoline) or the like.

The product of this reaction is a compound of the formula

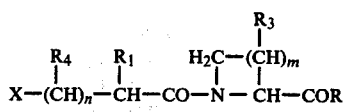 (X)

The product of formula X is subjected to a displacement reaction with the anion of a thioacid of the formula (VII) $R_2$—SH yielding a product of the formula

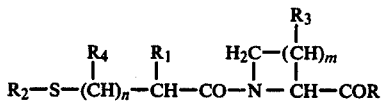 (XI)

When $R_2$ is $R_5CO$, this product can then be converted to the product

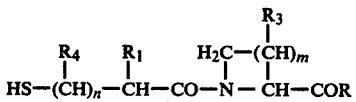 (XII)

by ammonolysis. When $R_2$ is a protecting group, then the compound of formula XII can be obtained by "deprotection" as described above. When R is an ester group (i.e., R is lower alkoxy), the ester group can be removed, e.g., when R is tert. butoxy or tert. amyloxy, by treatment of the ester of formula XI or XII with trifluoroacetic acid and anisole to give the corresponding free acid. When other alkoxy groups are present, alkaline hydrolysis will yeild the corresponding acid.

A variation of this procedure involves the use of an acrylic acid of the formula

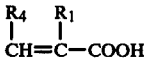 (VI)

as starting material. This acrylic acid is first converted to the acid halide form then made to react with a compound of formula III to obtain a compound of the formula

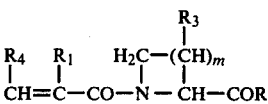 (XIII)

and this intermediate is subjected to the addition reaction with the thiol or thioacid VII as described above.

A tosyloxyalkanoic acid of the formula

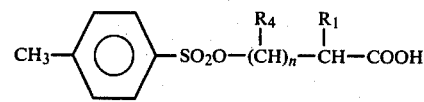 (XIV)

can also be used as the agent to acylate the acid of formula III, then the acylation product is subjected to the displacement reaction, etc., as described above.

The acrylic acid of formula VI can alternatively be first made to react with the thioacid of formula VII to obtain a product of the formula

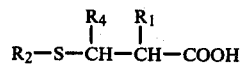 (XV)

which is converted to its acid halide, e.g., with thionyl chloride, then coupled to the compound of formula III and the same sequence as above then followed.

The acid or ester of formula III can also be acylated with a "protected" form of a ω-mercaptoalkanoic acid of the formula

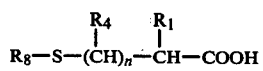 (XVI)

wherein $R_8$ is the "protecting" group. Such "protecting" groups can take the form described above.

Following the acylation, the product can be "deprotected" by one of the known methods referred to above.

Still another acylating agent can take the form of a thiolactone, e.g., β-propiothiolactone, α-methyl-β-propiothiolactone or the like.

Additional details of preferred modes of producing compounds of this invention can be found in the following and in the specific examples.

According to a particularly preferred modification, the acid or ester of formula III is acylated with a haloalkanoyl halide of the formula

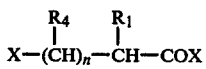 (XVII)

wherein each X is independently a halogen, preferably chlorine or bromine, $R_1$ is hydrogen, lower alkyl or phenyl-lower alkyl and n is 0, 1 or 2. This reaction is effected in an alkaline medium, e.g., dilute alkali metal hydroxide solution, alkali metal bicarbonate or alkali metal carbonate solution at a reduced temperature, e.g., about 0° to 15° C. The reaction product is subjected to displacement with the anion of the thiol or thio acid of the formula VII above, also in alkaline medium, preferably alkali metal carbonate solution, and then worked up in conventional manner. The product of this reaction, wherein $R_2$ of formula I is $R_5$—CO, is converted to the product wherein $R_2$ is hydrogen by ammonolysis, e.g., alcoholic ammonia or concentrated ammonium hydroxide solution, or alkaline hydrolysis, e.g., with aqueous metal hydroxide. When an acid of formula III is used as starting material, the final product obtained as the free carboxylic acid can then be converted to its ester, for example by esterification with a diazoalkane, like diazomethane, 1-alkyl-3-p-tolyl-triazene, like 1-n-butyl-3-p-tolyltriazene or the like. Treatment of an ester, preferably the methyl ester, with an alcoholic ammonia solution, converts the free acid to the amide, i.e., R is NH₂.

According to another variation, an ester, preferably the t-butyl ester, of formula III, in an anhydrous medium such as dichloromethane, tetrahydrofuran, dioxane or the like, is treated with a thioalkanoic acid of the formula

$$R_2-S-(CH_2)_n-\overset{R_1}{\underset{|}{C}H}-COOH \qquad (XVIII)$$

in the presence of dicyclohexylcarbodiimide, N,N'-carbonylbisimidazole, ethoxyacetylene, diphenylphosphoryl azide or similar coupling agents at a temperature in the range of about 0° to 10° C. The ester group (R) can then be removed, for example, by treatment with trifluoroacetic acid and anisole at about room temperature.

When an ester of formula III (e.g., R is lower alkoxy, especially, t-butoxy) is acylated with a thiolactone, e.g., β-propiothiolactone, α-methyl-β-propiothiolactone or the like, the reaction can be effected in an anhydrous solvent like tetrahydrofuran, dioxane, methylene chloride or the like at about 0° C. to about room temperature. The ester group can be removed with anisole and trifluoroacetic acid as described above.

In similar manner, when R₂ is

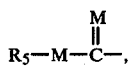

$$R_5-M-\overset{M}{\underset{\|}{C}}-,$$

products of formula I having this substituent are formed by reacting a compound of formula XII with the halogenated compound

$$R_5-M-\overset{M}{\underset{\|}{C}}-X \qquad (XIX)$$

or alternatively reacting a compound of formula X with an alkali metal salt or alkaline earth metal salt of the formula

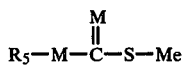

$$R_5-M-\overset{M}{\underset{\|}{C}}-S-Me \qquad (XX)$$

wherein Me represents the alkali metal or alkaline earth metal.

When R₂ is

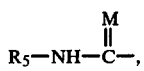

$$R_5-NH-\overset{M}{\underset{\|}{C}}-,$$

products of formula I having this substituent are produced by reacting a compound of formula XII with the appropriately substituted isocyanate or isothiocyanate of the formula (XXI) R₅—N=C=M Alternatively, the same products can be produced by coupling an acid of the formula

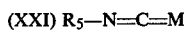

$$R_5-NH-\overset{M}{\underset{\|}{C}}-S-(CH)_n-\overset{R_1}{\underset{|}{C}}H-COOH \qquad (XXII)$$

with an amino acid of formula III.

Compounds of formula I, wherein R₂ is lower alkyl, phenyl, substituted phenyl, phenyl-lower alkyl, triphenyl-lower alkyl, lower alkylthiomethyl or phenyl-lower alkyl, triphenyl-lower alkyl, lower alkylthiomethyl or phenyl-lower alkylthiomethyl are produced by reacting a compound of formula XII with the corresponding halide R₂X or by reacting a compound of formula X with the corresponding thiol R₂SH in the same manner as described above.

When R₂ is lower alkanoylamidomethyl, the product of formula I is produced by condensing a compound of formula XII with the corresponding hydroxymethyl-lower alkanoylamide of the formula (XXIII) lower alkyl—CO—NHCH₂OH in the presence of an acid catalyst like trifluoroacetic acid.

Products of formula I wherein R₂ is R₆—S can be prepared by any of the known methods for the synthesis of mixed disulfides, e.g., by the reaction of a compound of formula (XII) with a thiosulfinate (XXIV), thiosulfonate (XXV), sulfenyl halide (XXVI), thiosulfate (XXVII) or sulfenyl thiocyanate (XXVIII)

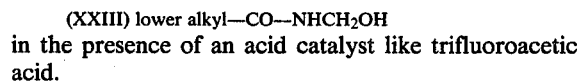

$$R_6-\overset{O}{\underset{\|}{S}}-S-R_6, \quad R_6-\overset{O}{\underset{\underset{\|}{\|}}{S}}-S-R_6,$$

(XXIV)   (XXV)

(XXVI) R₆S—X, (XXVII) R₆—S—SO₃H, (XXVIII) R₆—S—SCN

In the particular case wherein R₇ is

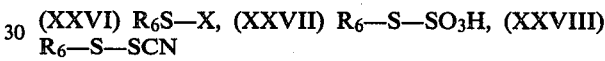

$$-S(O)_p-(CH)_n-\overset{R_1}{\underset{|}{C}}H-CO-\overset{R_4}{\underset{|}{N}}-\overset{CH_2-(CH)_n}{\underset{|}{C}H}-COR,$$

R, R₁, R₃ and R₄ are the same as the corresponding substituents in formula I and p is 0, the symmetrical disulfides can be obtained by direct oxidation of a compound of formula XII with iodine. When p is 1 or 2, such products are obtained by the stepwise oxidation of the corresponding compound wherein p is 0. Mixed disulfides are obtained by the modification shown in the examples.

Products of formula I have one or more asymmetric carbons. When R₁, R₃ or R₄ is other than hydrogen the carbon to which it is attached is asymmetric. These carbon atoms are indicated by an asterisk in formula I. The compounds accordingly exist in stereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form. Also the D-isomer with respect to the α-carbon in the acyl side chain (i.e., the carbon bearing R₁) is preferred.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen(renin)→angiotensin I→angiotensin II sequence by inhibiting angiotensin converting enzyme and reducing or eliminating the formation of the pressor substance angiotensin II. Thus by the administration of a composition containing one or a combination of compounds of formula I of physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneous, intramuscular, intravenous or intraperitoneal can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees celsius.

EXAMPLE 1

1-(2-Benzoylthioacetyl)-L-Proline

L-Proline (5.75 g.) is dissolved in N sodium hydroxide (50 ml.) and the solution is chilled in an ice-water bath. Sodium hydroxide 2 N (26 ml.) and chloroacetyl chloride (5.65 g.) are added and the mixture is stirred vigorously at room temperature for three hours. A suspension of thiobenzoic acid (7.5 g.) and potassium carbonate (4.8 g.) in water (50 ml.) is added. After 18 hours stirring at room temperature, the reaction mixture is acidified and extracted with ethyl acetate. The ethyl acetate layer is washed with water, dried over magnesium sulfate and concentrated to dryness in vacuo. The residue (14.6 g.) is dissolved in ethyl acetate (150 ml.) and dicyclohexylamine (11 ml.) is added. The crystals are filtered and recrystallized from ethyl acetate, yield 5.7 g. m.p. 151°-152°. To convert the salt to the acid, the crystals are dissolved in a mixture of 5% aqueous potassium bisulfate (100 ml.) and ethyl acetate (300 ml.). The organic phase is washed once with water, dried over magnesium sulfate and concentrated to dryness in vacuo, yield 3.45 g.

EXAMPLE 2

1-(2-Mercaptoacetyl)-L-Proline 1-(2-Benzoylthioacetyl)-L-proline (3.4 g.) is dissolved in a mixture of water (10.5 ml.) and concentrated ammonia (6.4 ml.). After one hour, the reaction mixture is diluted with water and filtered. The filtrate is extracted with ethyl acetate and then acidified with concentrated hydrochloric acid, saturated with sodium chloride and extracted twice with ethyl acetate. The ethyl acetate extracts are washed with saturated sodium chloride and concentrated to dryness, yield 1.5 g. The product, 1-(2-mercaptoacetyl)-L-proline is crystallized from ethyl acetate (m.p. 133°-135°).

EXAMPLE 3

1-(2-Benzoylthioacetyl)-L-Proline Methyl Ester 1-(2-Benzoylthioacetyl)-L-proline obtained in Example 1, is dissolved in methanol and an ethereal solution of diazomethane is added until there is a persistent yellow color. After 15 minutes, a few drops of acetic acid are added and the solvent is removed in vacuo to obtain 1-(2-benzoylthioacetyl)-L-proline methyl ester.

EXAMPLE 4

1-(2-Mercaptoacetyl)-L-Proline Amide

The product of Example 3 is dissolved in 10% methanolic ammonia and the solution is stored at room temperature in a pressure bottle. When thin layer chromatographic analysis indicates that the two ester functions have been ammonolyzed, the reaction mixture is concentrated to dryness to obtain 1-(2-mercaptoacetyl)-L-proline amide.

EXAMPLE 5

1-(2-Benzoylthioacetyl)-L-Hydroxyproline

By substituting L-hydroxyproline for the L-proline in the procedure of Example 1, 1-(2-benzoylthioacetyl)-L-hydroxyproline is obtained.

EXAMPLE 6

1-(2-Mercaptoacetyl)-L-Hydroxyproline

By treating the product of Example 5 with ammonia as in Example 2, 1-(-mercaptoacetyl)-L-hydroxyproline is obtained.

EXAMPLE 7

1-(2-Benzoylthioacetyl)-L-Azetidine-2-Carboxylic Acid

By substituting L-azetidine-2-carboxylic acid for the L-proline in the procedure of Example 1, 1-(2-benzoylthioacetyl)-L-azetidine-2-carboxylic acid is obtained.

EXAMPLE 8

1-(2-Mercaptoacetyl)-L-Azetidine-2-Carboxylic Acid

By treating the product of Example 7 with ammonia as in Example 2, 1-(2-mercaptoacetyl)-L-azetidine-2-carboxylic acid is obtained.

EXAMPLE 9

1-(2-Benzoylthioacetyl)-L-Pipecolic Acid

By substituting L-pipecolic acid for the L-proline in the procedure of Example 1, 1-(2-benzoylthioacetyl)-L-pipecolic acid is obtained.

EXAMPLE 10

1-(2-Mercaptoacetyl)-L-Pipecolic Acid

By treating the product of Example 9 with ammonia as in Example 2, 1-(2-mercaptoacetyl)-L-pipecolic acid is obtained.

EXAMPLE 11

1-(2-Benzoylthiopropanoyl)-L-Proline

L-Proline (5.75 g.) is dissolved in aqueous N sodium hydroxide (50 ml.) and the solution is chilled in an ice bath with stirring. 2 N sodium hydroxide (25 ml.) and 2-bromopropionyl chloride (8.57 g.) are added in that order and the mixture is removed from the ice bath and stirred at room temperature for one hour. A mixture of thiobenzoic acid (7.5 g.) and potassium carbonate (4.8 g.) in water (50 ml.) is added and the mixture is stirred overnight at room temperature. After acidification with concentrated hydrochloric acid, the aqueous solution is extracted with ethyl acetate and the organic phase is washed with water, dried and concentrated to dryness. The residue (14.7 g.) is chromatographed on a column of 440 g. of silica gel with a mixture of benzene-acetic acid (7:1). The fractions containing the desired material are pooled, concentrated to dryness, and the residue is precipitated twice with ether-hexane and converted to a dicyclohexylamine salt in ether-hexane, yield 9.4 g. m.p., (142) 148°–156°. The dicyclohexylamine salt is converted back to the acid as in Example 1, yield 5.7 g.

EXAMPLE 12

1-(2-Mercaptopropanoyl)-L-Proline 1-(2-Benzoylthiopropanoyl)-L-proline (5.7 g.) is dissolved in a mixture of water (12 ml.) and concentrated ammonium hydroxide (9 ml.) with stirring. After one hour, the mixture is diluted with water (10 ml.) and filtered. The filtrate is extracted twice with ethyl acetate, concentrated to one-third of the original volume, acidified with concentrated hydrochloric acid and extracted with ethyl acetate. The organic phase is washed with saturated sodium chloride, dried and concentrated to dryness in vacuo. The residue, 1-(2-mercaptopropanoyl)-L-proline, is crystallized from ethyl acetate-hexane, yield 3 g., m.p. (105) 116°–120°.

EXAMPLE 13

1-(3-Benzoylthiopropanoyl)-L-Proline

L-Proline (5.75 g.) is dissolved in normal sodium hydroxide (50 ml.) and the solution is chilled in an ice bath. 3-Bromopropionyl chloride (8.5 g.) and 2 N sodium hydroxide (27 ml.) are added and the mixture is stirred for 10 minutes in the ice bath and three hours at room temperature. A suspension of thiobenzoic acid (7.5 g.) and potassium carbonate (4.5 g.) in water (50 ml.) is added and the mixture is stirred for 18 hours at room temperature. After acidification with concentrated hydrochloric acid, the aqueous phase is extracted twice with ethyl acetate. The organic layers are dried over magnesium sulfate and concentrated to dryness in vacuo to obtain 1-(3-benzoylthiopropanoyl)-L-proline, yield 7.1 g., m.p. 101°–102° (ethyl acetate-hexane).

EXAMPLE 14

L-Proline tert.-butyl ester

L-Proline (230 g.) is dissolved in a mixture of water (1 l.) and 5 N sodium hydroxide (400 ml.). The solution is chilled in an ice bath, and under vigorous stirring, 5 N sodium hydroxide (460 ml.) and benzyloxycarbonyl chloride (340 ml.) are added in five equal aliquots during a half hour period. After one hour stirring at room temperature, the mixture is extracted twice with ether and acidified with concentrated hydrochloric acid. The precipitate is filtered and dried. Yield 442 g. m.p. 78°–80°.

The benzyloxycarbonyl-L-proline thus obtained (180 g.) is dissolved in a mixture of dichloromethane (300 ml.), liquid isobutylene (800 ml.) and concentrated sulfuric acid (7.2 ml.). The solution is shaken in a pressure bottle for 72 hours. The pressure is released, the isobutylene is allowed to evaporate and the solution is washed with 5% sodium carbonate, water, dried over magnesium sulfate and concentrated to dryness in vacuo, to obtain benzyloxycarbonyl-L-proline tert.butyl ester, yield 205 g.

Benzyloxycarbonyl-L-proline tert.butyl ester (205 g.) is dissolved in absolute ethanol (1.2 l) and hydrogenated at normal pressure with 10% Pd on carbon (10 g.) until only a trace of carbon dioxide is observed in the hydrogen exit gas (24 hours). The catalyst is filtered off and the filtrate is concentrated in vacuo at 30 mm. Hg. The residue is distilled in vacuo, to obtain L-proline tert.butyl ester, b.p.$_{1mm}$ 50°–51°.

EXAMPLE 15

1-(3-Acetylthiopropanoyl)-L-Proline tert-butyl Ester

L-Proline tert-butyl ester (5.13 g.) is dissolved in dichloromethane (40 ml.) and the solution is chilled in an ice-water bath. A solution of dicyclohexylcarbodiimide (6.18 g.) in dichloromethane (20 ml.) is added followed immediately by 3-acetylthiopropanoic acid (4.45 g.). After 15 minutes stirring in the ice-water bath and 16 hours at room temperature, the precipitate is filtered off and the filtrate is concentrated to dryness in vacuo. The residue is dissolved in ethyl acetate and washed neutral. The organic layer is dried over magnesium sulfate and concentrated to dryness in vacuo to obtain 9.8 g. of 1-(3-acetylthiopropanoyl)-L-proline tert-butyl ester.

EXAMPLE 16

1-(3-Acetylthiopropanoyl)-L-Proline 1-(3-Acetylthiopropanoyl)-L-proline-t-butyl ester (4.7 g.) is dissolved in a mixture of anisole (34 ml.) and trifluoroacetic acid (68 ml.) and the mixture is kept at room temperature for one hour. The solvents are removed in vacuo and the residue is precipitated from ether-hexane several times. The residue (3.5 g.) is dissolved in acetonitrile (25 ml.) and dicyclohexylamine (2.8 ml.) is added. The crystalline salt is filtered and recrystallized from isopropanol. Yield 3.8 g.. m.p. 176°–177°. The salt is reconverted to 1-(3-acetylthiopropanoyl)-L-proline as in Example 1, yield 1.25 g., m.p. 89°–90° (ethyl acetate-hexane).

EXAMPLE 17

1-(3-Mercaptopropanoyl)-L-Proline tert-butyl Ester

To a solution of L-proline tert-butyl ester (3.42 g.) in dry tetrahydrofuran (10 ml.) chilled in an ice bath, propiothiolactone (1.76 g.) is added. After 5 minutes storage in the ice bath and three hours at room temperature, the reaction mixture is diluted with ethyl acetate (200 ml.) and washed with 5% potassium bisulfate, and water. The organic layer is dried over magnesium sulfate and concentrated to dryness in vacuo. The residue 1-(3-mercaptopropanoyl)-L-proline tert-butyl ester is crystallized from ether-hexane, yield 3.7 g., m.p. 57°–58°.

EXAMPLE 18

1-(3-Mercaptopropanoyl)-L-Proline

Procedure A 1-(3-Benzoylthiopropanoyl)-L-proline (4.9 g.) is dissolved in a mixture of water (8 ml.) and concentrated ammonium hydroxide (5.6 ml.) and the solution is stored with stirring under argon for one hour. The reaction mixture is diluted with water, filtered, and the filtrate is extracted with ethyl acetate. The aqueous phase is acidified with concentrated hydrochloric acid, saturated with sodium chloride and extracted with ethyl acetate. The organic layers are washed with saturated sodium chloride, dried over magnesium sulfate, and concentrated to dryness in vacuo. The residue, 1-(3-mercaptopropanoyl)-L-proline, is crystallized from ethyl acetate hexane, yield 2.5 g., m.p. 68°–70°.

Procedure B 1-(3-Acetylthiopropanoyl)-L-proline (0.8 g.) is dissolved in 5.5 N methanolic ammonia (5 ml.) and the solution kept under argon at room temperature. After 2 hours the solvent is removed in vacuo, the residue is dissolved in water and applied to an ion exchange column on the H$^+$ cycle [Dowex 50(Analytical grade)] and eluted with water. The fractions that give thiol positive reaction are pooled and concentrated to dryness, yield 0.6 g. This product is crystallized from ethyl acetate-hexane as in Procedure A to obtain 1-(3-mercaptopropanoyl)-L-proline.

Procedure C 1-(3-Mercaptopropanoyl)-L-proline t-butyl ester (2.3 g.) is dissolved in a mixture of anisole (20 ml.) and trifluoroacetic acid (45 ml.). After one hour storage at room temperature under argon, the reaction mixture is concentrated to dryness in vacuo and the residue precipitated from ethyl acetate-hexane several times. The residue (1.9 g.) is dissolved in ethyl acetate (30 ml.) and dicyclohexylamine (1.85 ml.) is added. The crystalline salt is filtered and recrystallized from isopropanol, yield 2 g. m.p. 187°–188°.

The salt is converted to the acid as in Example 1, yield 1.3 g. The product is crystallized from ethyl acetate hexane as in Procedure A.

Salts

Sodium 1-(3-Mercaptopropanoyl)-L-proline (500 mg.) is dissolved in a mixture of water (2.5 ml.) and N sodium hydroxide (2.5 ml.). The solution is freeze dried to obtain the sodium salt.

Magnesium 1-(3-Mercaptopropanoyl)-L-proline (500 mg.), magnesium oxide (49.5 mg.), and water (10 ml.) are stirred with slight heating until complete solution is obtained. Then the solvent is removed by freeze drying to obtain the magnesium salt.

Calcium 1-(3-Mercaptopropanoyl)-L-proline (500 mg.) is dissolved in a mixture of calcium hydroxide (91 mg.) and water (10 ml.), and the solution is freeze dried to obtain the calcium salt.

Potassium 1-(3-Mercaptopropanoyl)-L-proline (500 mg.) is dissolved in a mixture of potassium bicarbonate (246 mg.) and water (10 ml.) and freeze dried to obtain the potassium salt.

N-Methyl-Glucamine 1-(3-Mercaptopropanoyl)-L-proline (500 mg.) and N-methyl-D-glucamine (480 mg.) are dissolved in water (10 ml.) and freeze dried to obtain the N-methyl-D-glucamine salt.

EXAMPLE 19

1-(3-Mercaptopropanoyl)-L-Hydroxyproline

By substituting L-hydroxyproline for the L-proline in the procedure of Example 11 and then treating the product by Procedure A of Example 18, 1-(3-benzoylthiopropanoyl)-L-hydroxyproline and 1-(3-mercaptopropanoyl)-L-hydroxyproline, respectively, are obtained.

EXAMPLE 20

1-(3-Mercaptopropanoyl)-L-Azetidine-2-Carboxylic Acid

By substituting L-azetidine-2-carboxylic acid tert-butyl ester (prepared by substituting L-azetidine-2-carboxylic acid for the proline in Example (14) for the L-proline tert-butyl ester in the procedure of Example 15, treating the product as in Example 16 and the 1-(3-acetylthiopropanoyl)-L-azetidine-2-carboxylic acid thus obtained by Procedure B of Example 18, 1-(3-acetylthiopropanoyl)-L-azetidine-2-carboxylic acid tert-butyl ester and 1-(3-mercaptopropanoyl)-L-azetidine-2-carboxylic acid, respectively, are obtained.

EXAMPLE 21

1-(3-Mercaptopropanoyl)-L-Pipecolic Acid

By substituting L-pipecolic acid tert-butyl ester (prepared by substituting L-pipecolic acid for the L-proline in Example 14) for the L-proline tert-butyl ester in the procedure of Example 15 and treating the product by Procedure C of Example 18, 1-(3-mercaptopropanoyl)-L-pipecolic acid tert-butyl ester and 1-(3-mercaptopropanoyl)-L-pipecolic acid, respectively, are obtained.

EXAMPLE 22

1-(3-Mercaptopropanoyl)-4-Methyl-L-Proline

By substituting 4-methyl-L-proline for L-proline in the procedure of Example 13 and then treating the product by Procedure A of Example 18, 1-(3-benzoylthiopropanoyl)-4-methyl-L-proline and 1-(3-mercaptopropanoyl)-4-methyl-L-proline, are obtained.

EXAMPLE 23

1-(3-Mercaptopropanoyl)-5-Hydroxy-L-Pipecolic Acid

By substituting 5-hydroxy-L-pipecolic acid for L-proline in the procedure of Example 13 and then treating the product by the Procedure A of Example 18, 1-(3-benzoylthiopropanoyl)-5-hydroxy-L-pipecolic, and 1-(3-mercaptopropanoyl)-5-hydroxy-L-pipecolic acid are obtained.

EXAMPLE 24

1-(3-Mercaptopropanoyl)-D-Proline

By substituting D-proline for L-proline in the procedure of Example 13 and then treating the product by Procedure A of Example 18, 1-(3-benzoylthiopropanoyl)-D-proline and 1-(3-mercaptopropanoyl)-D-proline, m.p. 68°–70°, are obtained.

EXAMPLE 25

3-Acetylthio-2-Methylpropanoic Acid

A mixture of thioacetic acid (50 g.) and methacrylic acid (40.7 g.) is heated on the steam bath for one hour and then stored at room temperature for 18 hours. After confirming by nmr spectroscopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

EXAMPLE 26

3-Benzoylthio-2-Methylpropanoic Acid

By substituting thiobenzoic acid for the thioacetic acid in the procedure of Example 25, 3-benzoylthio-2-methylpropanoic acid is obtained.

EXAMPLE 27

3-Phenylacetylthio-2-Methylpropanoic Acid

By substituting thiophenylacetic acid for the thioacetic acid in the procedure of Example 25, 3-phenylacetyl thio-2-methylpropanoic acid is obtained.

EXAMPLE 28

1-(3-Acetylthio-2-methylpropanoyl)-L-Proline tert-butyl Ester

L-Proline tert-butyl ester (5.1 g.) is dissolved in dichloromethane (40 ml.) and the solution stirred and chilled in an ice bath. Dicyclohexylcarbodiimide (6.2 g.) dissolved in dichloromethane (15 ml.) is added followed immediately by a solution of 3-acetylthio-2-methylpropanoic acid (4.9 g.) in dichloromethane (5 ml.). After 15 minutes stirring in the ice bath and 16 hours at room temperature, the precipitate is filtered off and the filtrate is concentrated to dryness in vacuo. The residue is dissolved in ethyl acetate and washed neutral. The organic phase is dried over magnesium sulfate and concentrated to dryness in vacuo. The residue 1-(3-acetylthio-2-methylpropanoyl)-L-proline tert-butyl ester is purified by column chromatography (silica gel-chloroform), yield 7.9 g.

EXAMPLE 29

1-(3-Acetylthio-2-methylpropanoyl)-L-Proline

Procedure A

The 1-(3-acetylthio-2-methylpropanoyl)-L-proline tert-butyl ester of Example 28 (7.8 g.) is dissolved in a mixture of anisole (55 ml.) and trifluoroacetic acid (110 ml.). After one hour storage at room temperature the solvent is removed in vacuo and the residue is precipitated several times from ether-hexane. The residue (6.8 g.) is dissolved in acetonitrile (40 ml.) and dicyclohexylamine (4.5 ml.) is added. The crystalline salt is boiled with fresh acetonitrile (100 ml.), chilled to room temperature and filtered, yield 3.8 g., m.p. (165) 187°–188°. This material is recrystallized from isopropanol $[\alpha]_D - 67°$ (C 1.4, EtOH). The crystalline dicyclohexylamine salt is suspended in a mixture of 5% aqueous potassium bisulfate and ethyl acetate. The organic phase is washed with water and concentrated to dryness. The residue is crystallized from ethyl acetate-hexane to yield the 1-(3-acetylthio-2-D-methylpropanoyl-L-proline, m.p. 83°–85° $[\alpha]_D^{25} - 162(c,1.7,EtOH)$.

Procedure B

3-Acetylthio-2-methylpropanoic acid (8.1 g.) and thionyl chloride (7 g.) are mixed and the suspension is stirred for 16 hours at room temperature. The reaction mixture is concentrated to dryness and distilled in vacuo (b.p. 80°). This 3-acetylthio-2-methylpropanoic acid chloride (5.4 g.) and 2 N sodium hydroxide (15 ml.) are added to a solution of L-proline (3.45 g.) in normal sodium hydroxide (30 ml.) chilled in an ice water bath. After 3 hours stirring at room temperature, the mixture is extracted with ether, the aqueous phase is acidified and extracted with ethyl acetate. The organic phase is dried over magnesium sulfate and concentrated to dryness to obtain 1-(3-acetylthio-2-DL-methylpropanoyl)-L-proline.

Procedure C

Methacryloyl chloride (4.16 g.) is added to a solution of L-proline (3.45 g.) in a mixture of water (100 ml.) and sodium bicarbonate (12 g.) chilled in an ice water bath, with vigorous stirring. When the addition is completed, the mixture is stirred at room temperature for two hours, and then extracted with ether. The aqueous phase is acidified with N hydrochloric acid and extracted with ethyl acetate. The organic phase is concentrated to dryness in vacuo, the residue is mixed with thiolacetic acid (3.5 g.), a few crystals of azobisisobutyronitrile are added and the mixture is heated on the steam bath for two hours. The reaction mixture is dissolved in benzene-acetic acid (75:25), and applied to a column of silica gel. Elution with the same solvent mixture yields the 1-(3-acetylthio-2-DL-methylpropanoyl)-L-proline.

EXAMPLE 30

1-(3-Benzoylthio-2-methylpropanoyl)-L-proline tert-butyl Ester

By substituting 3-benzoylthio-2-methylpropanoic acid for the 3-acetylthio-2-methylpropanoic acid in the procedure of Example 28, 1-(3-benzoylthio-2-methylpropanoyl)-L-proline tert.butyl ester is obtained.

EXAMPLE 31

1-(3-Phenylacetylthio-2-methylpropanoyl)-L-Proline tert-butyl Ester

By substituting 3-phenylacetylthio-2-methylpropanoic acid for the 3-acetylthio-2-methylpropanoic acid in the procedure of Example 28, 1-(3-phenylacetylthio-2-methylpropanoyl)-L-proline tert butyl ester is obtained.

EXAMPLE 32

1-(3-Benzoylthio-2-methylpropanoyl)-L-Proline

By substituting 1-(3-benzoylthio-2-methylpropanoyl)-L-proline tert-butyl ester for the 1-(3-acetylthio)-2-methylpropanoyl)-1-proline tert-butyl ester in Procedure A of Example 29, 1-(3-benzoylthio-2-methylpropanoyl)-L-proline is obtained.

EXAMPLE 33

1-(3-Phenylacetylthio-2-methylpropanoyl)-L-Proline

By substituting 1-(3-phenylacetylthio-2-methylpropanoyl)-L-proline tert-butyl ester for 1-(3-acetylthio-2-methylpropanoyl)-L-proline tert-butyl ester in Procedure A of Example 29, 1-(3-phenylacetylthio-2-methylpropanoyl)-L-proline is obtained.

EXAMPLE 34

1-(3-Mercapto-2-D-methylpropanoyl)-L-Proline 1-(3-Mercapto-2-D-methylpropanoyl)-L-proline is obtained by treating the product of each of Examples 29, 32 and 33 as follows:

The thioester (0.85 g.) is dissolved in 5.5 N methanolic ammonia and the solution is kept at room temperature for 2 hours. The solvent is removed in vacuo and the residue is dissolved in water, applied to a ion exchange column on the H+ cycle (Dowex 50, analytical grade) and eluted with water. The fractions that give positive thiol reaction are pooled and freeze dried. The residue is crystallized from ethyl acetate-hexane, yield 0.3 g. The 1-(3-mercapto-2-D-methylpropanoyl)-L-proline has m.p. 103°–104°, $[\alpha]_D-131$ (C,2,EtOH).

EXAMPLE 35

1-(3-Acetylthio-2-methylpropanoyl)-L-Proline Methyl Ester 1-(3-Acetylthio-2-methylpropanoyl)-L-proline is reacted with an ethereal solution of diazomethane according to the procedure described in Example 3 to obtain 1-(3-acetylthio-2-methylpropanoyl)-L-proline methyl ester.

EXAMPLE 36

1-(3-Mercapto-2-methylpropanoyl)-L-Proline amide

By substituting 1-(3-acetylthio-2-methylpropanoyl)-L-proline methyl ester in the procedure of Example 4, 1-(3-mercapto-2-methylpropanoyl)-L-proline amide is obtained.

EXAMPLE 37

3-Acetylthio-2-Benzylpropanoic Acid

By substituting 2-benzylacrylic acid for the methacrylic acid in the procedure of Example 25, 3-acetylthio-2-benzylpropanoic acid is obtained.

EXAMPLE 38

1-(3-Acetylthio-2-benzylpropanoyl)-L-Proline tert-butyl Ester

By substituting 3-acetylthio-2-benzylpropanoic acid for the 3-acetylthio-2-methylpropanoic acid in the procedure of Example 22, 1-(3-acetylthio-2-benzylpropanoyl)-L-proline tert-butyl ester is obtained.

EXAMPLE 39

1-(3-Acetylthio-2-benzylpropanoyl)-L-Proline

The product of Example 38 is substituted for the 1-(3-acetylthio-2-methylpropanoyl-L-proline tert-butyl ester in the Procedure A of Example 29 to obtain 1-(3-acetylthio-2-benzylpropanoyl)-L-proline.

EXAMPLE 40

1-(3-Mercapto-2-benzylpropanoyl)-L-Proline 1-(3-Acetylthio-2-benzylpropanoyl)-L-proline is treated with methanolic ammonia according to the procedure of Example 34 to obtain 1-(3-mercapto-2-benzylpropanoyl)-L-proline as an oil, $R_f=0.47$ (silica gel, benzene-acetic acid 75:25).

EXAMPLE 41

1-(3-Mercapto-2-methylpropanoyl)-L-Hydroxy Proline

By substituting L-hydroxy proline tert-butyl ester in the procedure of Example 28, treating the product according to Procedure A of Example 29 and then continuing as in Example 34, 1-(3-acetylthio-2-methylpropanoyl)-L-hydroxyproline tert-butyl ester, 1-(3-acetylthio-2-methylpropanoyl)-L-hydroxyproline and 1-(3-mercapto-2-methylpropanoyl)-L-hydroxyproline, respectively, are obtained.

EXAMPLE 42

1-(3-Mercapto-2-methylpropanoyl)-L-Azetidine-2-Carboxylic Acid

By substituting L-azetidine-2-carboxylic acid tert-butyl ester in the procedure of Example 28, treating the product according to Procedure A of Example 29 and then continuing as in Example 34, 1-(3-acetylthio-2-methylpropanoyl)-L-azetidine-2-carboxylic acid tert-butyl ester, 1-(3-acetylthio-2-methylpropanoyl)-L-azetidine-2-carboxylic acid and 1-(3-mercapto-2-methylpropanoyl)-L-azetidine-2-carboxylic acid are obtained.

EXAMPLE 43

1-(3-Mercapto-2-methylpropanoyl)-L-Pipecolic Acid

By substituting L-pipecolic acid in the procedure of Example 28, treating the product according to Procedure A of Example 29 and then continuing as in Example 34, 1-(3-acetylthio-2-methylpropanoyl)-L-pipecolic acid tert-butyl ester, 1-(3-acetylthio-2-methylpropanoyl)-L-pipecolic acid and 1-(3-mercapto-2-methylpropanoyl)-L-pipecolic acid, respectively, are obtained.

EXAMPLE 44

1-(4-Benzoylthiobutanoyl)-L-Proline

To a solution of L-proline (2.88 g.) in normal sodium hydroxide (25 ml.) chilled in an ice bath, 2 N sodium hydroxide (12.5 ml.) and 4-chlorobutyryl chloride (3.5 g.) are added. The reaction mixture is stirred at room temperature for 3.5 hours and a suspension of thiobenzoic acid (3.75 g.) and potassium carbonate (2.4 g.) in water (25 ml.) is added. After overnight stirring at room temperature, the reaction mixture is acidified with concentrated hydrochloric acid and extracted with ethyl acetate. The organic layer is dried over magnesium sulfate and concentrated to dryness in vacuo. The residue is chromatographed on a column of silica gel with benzene-acetic acid (7:1). The fractions containing the desired material are pooled and concentrated to dryness, yield 1.35 g. A small aliquot of this material is dissolved in ethyl acetate and dicyclohexylamine is added until pH 8-10 (on a wet pH paper). The dicyclohexylamine salt crystallizes out, immediately, m.p. 159°-161°.

EXAMPLE 45

1-(4-Mercaptobutanoyl)-L-Proline 1-(4-Benzylthiobutanoyl)-L-proline (1.08 g.) is dissolved in a mixture of water (4 ml.) and concentrated ammonia (2.7 ml.). After one hour stirring at room temperature, the mixture is diluted with water, filtered, extracted with ethyl acetate, and the aqueous phase is concentrated in vacuo. This ammonium salt of 1-(4-mercaptobutanoyl)-L-proline is purified by ion exchange chromatography on a column of diethylaminoethyl-Sephadex (cross linked dextran) with a gradient of ammonium bicarbonate, yield 0.7 g. The ammonium salt is dissolved in water (2 ml.) and applied to a column of Dowex 50 sulfonic acid resin analytical grade in the hydrogen form, and the free acid is eluted with water. The fractions containing the desired material (sulfhydryl reagent and carboxyl reagent positive) are pooled and freeze dried to obtain 1-(4-mercaptobutanoyl)-L-proline. The dicyclohexyl ammonium salt is produced by the procedure of Example 44, m.p. 157°-158°.

EXAMPLE 46

4-Bromo-2-Methylbutanoic Acid

Ethyl-4-bromo-2-methylbutanoate [G. Jones and J. Wood, Tetrahedron, 21, 2961 (1965)] (1.04 g.) is dissolved in dichloromethane (50 ml.) and cooled to $-10°$. A 1 M solution of boron tribromide in dichloromethane (50 ml.) is added dropwise with stirring and the stirring is continued for 1 hour at $-10°$ and 2 hours at 25°. The reaction is terminated by the careful addition of water. The layers are separated and the organic phase is washed with water, dried and concentrated to dryness to obtain 4-bromo-2-methylbutanoic acid.

EXAMPLE 47

1-(4-Benzoylthio-2-methylbutanoyl)-L-Proline (a) 4-Bromo-2-methylbutanoic acid (8 g.) and thionyl chloride (7 g.) are mixed and the mixture is stirred for 16 hours at room temperature. The reaction mixture is concentrated to dryness and distilled in vacuo.

(b) To a solution of L-proline (2.88 g.) in normal sodium hydroxide (25 ml.) chilled in an ice bath, 2 N sodium hydroxide (12.5 ml.) and the 4-bromo-2-methylbutanoic acid chloride obtained in part (a) (3.9 g.) are added. The reaction mixture is stirred at room temperature for 3.5 hours and a suspension of thiobenzoic acid (3.75 g.) and potassium carbonate (2.4 g.) in water (25 ml.) is added. After overnight stirring at room temperature, the reaction mixture is acidified with concentrated hydrochloric acid and extracted with ethyl acetate. The organic layer is dried over magnesium sulfate and concentrated to dryness in vacuo. The residue is chromatographed on a column of silica gel with benzene-acetic acid (7:1). The fractions containing the desired product, 1-(4-benzoylthio-2-methylbutanoyl)-L-proline are pooled and concentrated to dryness in vacuo.

EXAMPLE 48

1-(4-Mercapto-2-methylbutanoyl)-L-Proline

By substituting 1-(4-benzoylthio-2-methylbutanoyl)-L-proline for the 1-(4-benzoylthiobutanoyl)-L-proline in the procedure of Example 45, 1-(4-mercapto-2-methylbutanoyl)-L-proline is obtained.

EXAMPLE 49

4-Bromo-2-benzylbutanoic acid

By substituting ethyl-4-bromo-2-benzylbutanoate [prepared by the procedure of G. Jones and J. Wood [Tetrahedron, 21, 2961 (1965) starting with diethylbenzylmalonate]] for the ethyl-4-bromo-2-methylbutanoate in the procedure of Example 46, 4-bromo-2-benzylbutanoic acid is obtained.

EXAMPLE 50

1-(4-Benzoylthio-2-benzylbutanoyl)-L-Proline

By substituting 4-bromo-2-benzylbutanoic acid for the 4-bromo-2-methylbutanoic acid in the procedure of Example 47, 1-(4-benzoylthio-2-benzylbutanoyl)-L-proline is obtained.

EXAMPLE 51

1-(4-Mercapto-2-benzylbutanoyl)-L-Proline

By substituting 1-(4-benzoylthio-2-benzylbutanoyl)-L-proline for the 1-(4-benzoylthiobutanoyl)-L-proline in the procedure of Example 45, 1-(4-mercapto-2-benzylbutanoyl)-L-proline is obtained.

EXAMPLE 52

1-(4-Mercaptobutanoyl)-L-Hydroxyproline

By substituting L-hydroxyproline for the L-proline in the procedure of Example 44 and subjecting the product to ammonolysis as in Example 45, 1-(4-benzoylthiobutanoyl)-L-hydroxyproline and 1-(4-mercaptobutanoyl)-L-hydroxyproline, respectively, are obtained.

EXAMPLE 53

1-(4-Mercaptobutanoyl)-L-Azetidine-2-Carboxylic Acid

By substituting L-azetidine-2-carboxylic acid for the L-proline in the procedure of Example 44 and subjecting the product to ammonolysis as in Example 45, 1-(4-benzoylthiobutanoyl)-L-azetidine-2-carboxylic acid and 1-(4-mercaptobutanoyl)-L-azetidine-2-carboxylic acid, respectively, are obtained.

EXAMPLE 54

1-(4-Mercaptobutanoyl)-L-Pipecolic Acid

By substituting L-pipecolic acid for the L-proline in the procedure of Example 44 and subjecting the product to ammonolysis as in Example 45, 1-(4-benzoylthiobutanoyl)-L-pipecolic acid and 1-(4-mercaptobutanoyl)-L-pipecolic acid, respectively, are obtained.

EXAMPLE 55

1-(3-Acetylthiobutanoyl)-L-Proline tert-butyl Ester

Dicyclohexylcarbodiimide (6.2 g.) and 3-acetylthiobutyric acid (4.86 g.) are added to a solution of L-proline tert-butyl ester (5.1 g.) in dichloromethane (60 ml.) stirred in an ice bath. After 15 minutes the ice bath is removed and the mixture is stirred at room temperature for 16 hours. The precipitate is filtered, the filtrate is concentrated to dryness and the residue is chromatographed on a column of silica gel with chloroform to obtain 1-(3-acetylthiobutanoyl)-L-proline tert-butyl ester, yield 5.2 g.

EXAMPLE 56

1-(3-Acetylthiobutanoyl)-L-Proline

The 1-(3-acetylthiobutanoyl)-L-proline tert-butyl ester of Example 55 (5.2 g.) is dissolved in a mixture of trifluoroacetic acid (60 ml.) and anisole (30 ml.) and the solution is kept at room temperature for one hour. The solvents are removed in vacuo and the residual 1-(3-acetylthiobutanoyl)-L-proline is reprecipitated from ether-hexane several times, yield 4 g.. The dicyclohexylamine salt is made by the procedure of Example 44, m.p. 175°–176°.

EXAMPLE 57

1-(3-Mercaptobutanoyl)-L-Proline

The 1-(3-acetylthiobutanoyl)-L-proline of Example 56 (0.86 g.) is dissolved in 5.5 N. methanolic ammonia (20 ml.) and the reaction mixture is stored at room temperature for 2 hours. The solvent is removed in vacuo and the residue chromatographed on an ion exchange column (Dowex 50) with water. The fractions containing the desired 1-(3-mercaptobutanoyl)-L-proline are pooled and lyophilized, yield 0.6 g. The dicyclohexylamine salt is produced by the procedure of Example 44, m.p. 183°–184°.

EXAMPLE 58

1-[3-[[(Ethoxy)carbonyl]thio]propanoyl]-L-Proline

Ether chloroformate (1.2 g.) is added to a solution of 3-mercaptopropanoyl-L-proline [2.03 g.) in normal sodium bicarbonate (30 ml.) and the mixture is stirred vigorously at 5° for one hour, and for two hours at room temperature. After acidification with concentrated hydrochloric acid, the mixture is extracted with ethyl acetate. The organic phase is washed with water, dried over magnesium sulfate, and concentrated to dryness to yield 1-[3-[[(ethoxy)carbonyl]thio]propanoyl]-L-proline.

EXAMPLE 59

1-[3-[[(Ethoxy)thiocarbonyl]thio]propanoyl]-L-Proline

Aqueous 2 N sodium hydroxide (25 ml) and 3-bromopropionyl chloride (8.5 g) are added to a solution of L-proline (5.75 g) in N sodium hydroxide (50 ml) chilled and stirred in an ice bath. After five minutes the ice bath is removed and the stirring is continued at room temperature. After three hours ethyl xantogenic acid potassium salt (9.6 g) is added and the mixture is stirred overnight at room temperature. The solution is acidified with concentrated hydrochloric acid and extracted with ethyl acetate. The organic layer is concentrated to dryness and the residue is chromatographed on a column of silica gel with a mixture of benzene-acetic acid (7:1) as solvent, to yield 1-[3-[[(ethoxy)thiocarbonyl]thio]propanoyl]-L-proline, m.p. 94°–95°.

EXAMPLE 60

1-[3-[[(Benzylthio)carbonyl]thio]propanoyl]-L-Proline

A solution of benzylthiocarbonyl chloride (11 ml) in dioxane (20 ml) is added in five portions to a solution of 1-(3-mercaptopropanoyl)-L-proline (1.6 g) in normal sodium bicarbonate (24 ml) chilled in an ice bath, over a period of 30 minutes. The ice bath is removed and the stirring is continued for 2.5 hours at room temperature. After acidification with concentrated hydrochloric acid, the aqueous phase is extracted with ethyl acetate. The organic phase is dried over magnesium sulfate and concentrated to dryness to yield 1-[3-[[(benzylthio)carbonyl]thio]propanoyl]-L-proline.

EXAMPLE 61

1-[3-[[(Ethylthio)thiocarbonyl]thio]propanoyl]-L-Proline

Aqueous 2 N sodium hydroxide (25 ml) and 3-bromopropionyl chloride (8.5 g) are added to a solution of L-proline (5.75 g) in N sodium hydroxide (50 ml) chilled and stirred in an ice bath. After five minutes, the ice bath is removed and the stirring is continued at room temperature. After three hours, ethyl trithiocarbonate potassium salt (10.5 g) is added and the mixture is stirred at room temperature overnight. After acidification with concentration hydrochloric acid, the mixture is extracted with ethyl acetate. The organic layer is dried over magnesium sulfate and concentrated to dryness to yield 1-[3-[[(ethylthiothiocarbonyl]thio]propanoyl]-L-proline.

EXAMPLE 62

3-[[(Methylamino)thiocarbonyl]thio]propanoic acid

Methylisothiocyanate (4 g) is added to a solution of 3-mercaptopropanoic acid (5.3 g) in a mixture of pyridine (250 ml) and 0.5 N sodium hydroxide (100 ml). The solution is kept at 40° for two hours and concentrated to dryness in vacuo. The residue is dissolved in water (100 ml.), acidified with concentrated hydrochloric acid and extracted with ether. The organic phase is concentrated to dryness to yield 3-[[(methylamino)thiocarbonyl]thio]propanoic acid, m.p. 86°–87°.

EXAMPLE 63

1-[3-[[(Methylamino)thiocarbonyl]thio]propanoyl]-L-Proline tert-butyl ester

To a solution of L-proline tert-butyl ester (1.71 g) and hydroxybenzotriazole (1.35 g) in dichloromethane (10 ml) chilled and stirred in an ice bath, dicyclohexylcarbodiimide (2.06 g) and 3-[[methylamino)thiocarbonyl]thio]propanoic acid (1.79 g) are added. After 15 minutes, the bath is removed and the stirring is continued overnight. The precipitate is filtered off and the filtrate is diluted with ethyl acetate and washed neutral. The organic phase is concentrated to dryness to yield 1-[3-[[(methylamino)thiocarbonyl]thio]propanoyl]-L-proline tert-butyl ester, m.p. 129°–130°.

EXAMPLE 64

1-[3-[[(Methylamino)thiocarbonyl]thio]propanoyl]-L-Proline (A) 3-[3-[[(Methylamino)thiocarbonyl]thio]propanoyl]-L-proline tert-butyl ester (0.98 g) is dissolved in a mixture of anisole (3.6 ml) and trifluoroacetic acid (7.5 ml). After one hour at room temperature the mixture is concentrated to dryness in vacuo and the residue precipitated from ether-hexane three times. This material is chromatographed on a column of silica gel with a solvent mixture of benzene-acetic acid (75:25) to yield 1-[3-[[(methylamino)thiocarbonyl]thio]propanoyl]-L-proline, $R_f=0.4$ [silica gel-benzene:acetic acid (75:25)]. The dicyclohexylammonium salt has m.p. 127°–129°.

(B) Methylisothiocyanate (4 g) is added to a solution of 3-mercaptopropanoyl-L-proline (10.1 g) in a mixture of pyridine (250 ml) and 0.5 N sodium hydroxide (100 ml). The solution is kept at 40° for two hours and concentrated to dryness in vacuo. The residue is dissolved in water (100 ml), acidified with concentrated hydrochloric acid and extracted with ethyl acetate. The organic phase is concentrated to dryness to yield 1-[3-[[(methylamino)thiocarbonyl]thio]propanoyl]-L-proline.

EXAMPLE 65

1-[3-[[(Ethylamino)carbonyl]thio]propanoyl]-L-Proline

Ethylisocyanate (0.45 ml) is added to a solution of 1-(3-mercaptopropanoyl)-L-proline (1 g) in a mixture of N sodium hydroxide (5 ml) and pyridine (5 ml). The solution is heated at 40° for four hours and concentrated in vacuo. The residue is distributed between 0.1 N hydrochloric acid and ethyl acetate. The organic layer is washed with water, dried over magnesium sulfate and concentrated to dryness to yield 1-[3-[[(ethylamino)carbonyl]thio]propanoyl]-L-proline. The dicyclohexylammonium salt is prepared by adding dicyclohexylamine to a solution of the free acid in ethyl acetate, m.p. 150°–152°.

EXAMPLE 66

1-[3-[[(Ethoxy)carbonyl]thio]-2-methylpropanoyl]-L-Proline

By substituting 1-(3-mercapto-2-methylpropanoyl)-L-proline for the 3-mercaptopropanoyl-L-proline in the procedure of Example 58, 1-[3-[[(ethoxy)carbonyl]thio]-2-methylpropanoyl]-L-proline is obtained.

EXAMPLE 67

1-[3-[[(Ethoxy)carbonyl]thio]butanoyl]-L-Proline

By substituting 1-[3-mercaptobutanoyl)-L-proline for the 3-mercaptopropanoyl-L-proline in he procedure of Example 58, 1-[3-[[(ethoxy)carbonyl]thio]butanoyl]-L-proline is obtained.

EXAMPLE 68

1-[3-[[(Ethoxy)thiocarbonyl]thio]propanoyl]-L-Azetidine-2-Carboxylic Acid

By substituting L-azetidine-2-carboxylic acid for L-proline in the procedure of Example 59, 1-[3-[[(ethoxy)thiocarbonyl]thio]propanoyl]-L-azetidine-2-carboxylic acid is obtained.

EXAMPLE 69

1-[3-[[(Ethoxy)thiocarbonyl]thio]propanoyl]-L-Pipecolic acid

By substituting L-pipecolic acid for L-proline in the procedure of Example 59, 1-[3-[[(ethoxy)thiocarbonyl]thio]propanoyl]-L-pipecolic acid is obtained.

EXAMPLE 70

1-[4-[[(Benzylthio)carbonyl]thio]butanoyl]-L-Proline

By substituting 4-mercaptobutanoyl-L-proline for the 3-mercaptopropanoyl-L-proline in the procedure of Example 60, 1-[4-[[(benzylthio)carbonyl]thio]butanoyl]-L-proline is obtained.

EXAMPLE 71

1-[2-[[(Benzylthio)carbonyl]thio]propanoyl]-L-Proline

By substituting 2-mercaptopropanoyl-L-proline for the 3-mercaptopropanoyl-L-proline in the procedure of Example 60, 1-[2-[[(benzylthio)carbonyl]thio]propanoyl]-L-proline is obtained.

EXAMPLE 72

1-[3-[[(Ethylthio)thiocarbonyl]thio]propanoyl]-L-Proline methyl ester

A solution of 1-[3-[[(ethylthio)thiocarbonyl]thio]propanoyl]-L-proline in ethyl acetate is treated with an ethereal solution of diazomethane until persistent yellow color. After discharging the yellow color with a few drops of acetic acid, the solvents are removed in vacuo to yield 1-[3-[[(ethylthio)thiocarbonyl]thio]propanoyl]-L-proline methyl ester.

EXAMPLE 73

1-[3-[[(Methylamino)thiocarbonyl]thio]propanoyl]-5-hydroxy-L-Pipecolic acid

By substituting 1-[3-mercaptopropanoyl)-5-hydroxy-L-pipecolic acid for the 3-mercaptopropanoyl-L-proline in the Procedure B of Example 64, 1-[3-[[(methylamino)thiocarbonyl]thio]propanoyl]-5-hydroxy-L-pipecolic acid is obtained.

EXAMPLE 74

1-[3-[[(Methylamino)thiocarbonyl]thio]-2-methylpropanoyl]-L-Proline Amide

By substituting 1-(3-mercapto-2-methylpropanoyl)-L-proline amide for the 3-mercaptopropanoyl-L-proline in the Procedure B of Example 64, 1-[3-[[(methylamino)thiocarbonyl]thio]-2-methylpropanoyl]-L-proline amide is obtained.

EXAMPLE 75

1-[3-[[(Phenoxy)carbonyl]thio]propanoyl]-L-Proline

By substituting phenylchloroformate for ethyl chloroformate in the procedure of Example 58, 1-[3-[[(phenoxy)carbonyl]thio]propanoyl]-L-proline is obtained.

EXAMPLE 76

1-[3-[[(Phenoxy)carbonyl]thio]butanoyl]-L-Proline

By substituting phenylchloroformate for the ethyl chloroformate and 4-mercaptobutanoyl-L-proline for the 3-mercaptopropanoyl-L-proline in the procedure of Example 58, 1-[3-[[(phenoxy)carbonyl]thio]butanoyl]-L-proline is obtained.

EXAMPLE 77

1-[3-[[(Phenylamino)carbonyl]thio]propanoyl]-L-Proline

By substituting phenylisocyanate for the ethylisocyanate in the procedure of Example 65, 1-[3-[[(phenylamino)carbonyl]thio]propanoyl]-L-proline is obtained.

EXAMPLE 78

1-[3-[[(Phenethylamino)carbonyl]thio]propanoyl]-L-Proline

By substituting phenethylisocyanate for the ethylisocyanate in the procedure of Example 65, 1-[3-[[(phenethylamino)carbonyl]thio]propanoyl]-L-proline is obtained.

EXAMPLE 79

1-[3-[[(Ethylamino)carbonyl]thio]-2-benzylpropanoyl]-L-Proline

By substituting 1-(3-mercapto-2-benzylpropanoyl)-L-proline for the 1-(3-mercaptopropanoyl)-L-proline in the procedure of Example 65, 1-[3-[[(ethylamino)carbonyl]thio]-2-benzylpropanoyl]-L-proline is obtained.

EXAMPLE 80

1-(3-Methylthiopropanoyl)-L-Proline (A) Methyl 3-methylthiopropionate (51 g) is saponified with a 10% sodium hydroxide solution (150 ml, 30 minutes at 100°). The cooled solution is extracted with ether and then acidified. The crude acid thus obtained is distilled and converted to the acid chloride with thionyl chloride. A solution of L-proline (11.5 g) in N sodium hydroxide (100 cc) is chilled in an ice bath and the 3-methylthiopropanoic acid chloride (6.9 g) is added dropwise with vigorous stirring over a ten minute period. After five hours the reaction mixture is acidified and extracted with ethyl ether to yield 1-(3-methylthiopropanoyl)-L-proline. The dicyclohexylammonium salt is prepared by adding dicyclohexylamine to a solution of the free acid in ethyl acetate, m.p. 169°–171°.

(B) Methyl iodide (71 g) is added to a solution of 1-(3-mercaptopropanoyl)-L-proline ethyl ester (115 g) and sodium (11.5 g) in ethanol (400 ml). The reaction is allowed to proceed overnight, the ethanol is removed in vacuo and the residue is dissolved in a mixture of ethyl acetate and water. The organic layer is dried and concentrated to dryness in vacuo. The resulting 1-(3-methylthiopropanoyl)-L-proline ethyl ester (98 g) is suspended in a mixture of methanol (200 ml) and 5 N sodium hydroxide (200 ml) and stirred at room temperature for five hours. The methanol is removed in vacuo, and the aqueous phase is extracted with ethyl acetate, acidified and reextracted with ethyl acetate. This last organic phase is washed with water, dried and concentrated to dryness to yield 1-(3-methylthiopropanoyl)-L-proline.

EXAMPLE 81

1-[3-(4-Chlorophenylthio)propanoyl]-L-Proline

Aqueous 2 N sodium hydroxide (25 ml) and 3-bromopropionyl chloride (8.5 g) are added to a solution of L-proline (5.75 g) in N-sodium hydroxide (50 ml) chilled and stirred in an ice bath. After five minutes, the ice bath is removed and the stirring is continued for three hours at room temperature. The reaction mixture is acidified with concentrated hydrochloric acid and extracted with ethyl acetate. The organic layer is washed with water, dried and concentrated to dryness in vacuo. The residue is dissolved in a mixture of 4-chlorobenzenethiol (8 g), sodium hydroxide (4.2 g) and ethanol (300 ml). The solution is refluxed for 6 hours. The solvent is removed in vacuo and the residue is dissolved in water, acidified with concentrated hydrochloric acid and extracted with ethyl acetate. The organic layer is washed with water, dried, and concentrated to dryness in vacuo to yield 1-[3-(4-chlorophenylthio)propanoyl]-L-proline.

EXAMPLE 82

1-[[(3-Benzylthiomethyl)thio]propanoyl]-L-Proline 1-(3-Mercaptopropanoyl)-L-proline (8.1 g) is dissolved in boiling liquid ammonia (100 ml) and small pieces of sodium are added until permanent blue color is obtained which is then discharged with a small piece of ammonium chloride. Benzylthiomethyl chloride (6.9 g) is added and the ammonia is allowed to evaporate. The final traces of ammonia are removed in vacuo, the residue is dissolved in water and extracted with ethyl acetate. The aqueous phase is acidified with concentrated hydrochloric acid and extracted with ethyl acetate. The organic layer is washed with water, dried and concentrated to dryness to yield 1-[[(3-benzylthiomethyl)thio]propanoyl]-L-proline.

EXAMPLE 83

1-[[(3-Acetamidomethyl)thio]propanoyl]-L-Proline 1-(3-Mercaptopropanoyl)-L-proline (2 g) and N-hydroxymethylacetamide (0.89 g) are dissolved in trifluoroacetic acid (10 ml) and the solution is stored at room temperature for one hour. The excess trifluoroacetic acid is removed in vacuo and the residue is precipitated several times from ether-hexane. Finally, the residue is distributed between dilute hydrochloric acid and ethyl acetate. The organic layer is washed with water, dried and concentrated to dryness to yield 1-[[(3-acetamidomethyl)thio]propanoyl]-L-proline.

EXAMPLE 84

1-(Methylthioacetyl)-L-Proline

By substituting methyl methylthioacetate for the methyl 3-methylthiopropionate in the Procedure A of Example 80, 1-(methylthioacetyl)-L-proline, m.p. 123°–124°, is obtained.

EXAMPLE 85

1-(Benzylthioacetyl)-L-Proline

By substituting benzylthioacetyl chloride for the 3-methylthiopropanoyl chloride in the Procedure A of Example 80, 1-(benzylthioacetyl)-L-proline, m.p. 86°–88°, is obtained.

EXAMPLE 86

1-[3-[(2-Phenylethyl)thio]propanoyl]-L-Proline

By substituting phenethylbromide for the methyl iodide in the Procedure B of Example 80, 1-[3-[(2-phenylethyl)thio]propanoyl]-L-proline is obtained.

EXAMPLE 87

1-[3-[(Triphenylmethyl)thio]propanoyl]-L-Proline

By substituting triphenylmethyl chloride for the methyl iodide in the Procedure B of Example 80, 1-[3-[(triphenylmethyl)-thio]propanoyl]-L-proline is obtained.

EXAMPLE 88

1-(3-Methylthio-2-methylpropanoyl)-L-Proline Amide

By substituting 1-(3-mercapto-2-methylpropanoyl)-L-proline amide for the 1-(3-mercaptopropanoyl)-L-proline ethyl ester in the Procedure B of Example 80 and eliminating the saponification step, 1-(3-methylthio-2-methylpropanoyl)-L-proline amide is obtained.

EXAMPLE 89

1-(3-Methylthiopropanoyl)-L-Azetidine-2-Carboxylic Acid

By substituting L-azetidine-2-carboxylic acid for the L-proline in the Procedure A of Example 80, 1-(3-methylthiopropanoyl)-L-azetidine-2-carboxylic acid is obtained.

EXAMPLE 90

1-[3-(4-Methoxyphenylthio)propanoyl]-L-Proline

By substituting 4-methoxybenzenethiol for the 4-chlorobenzenethiol in the procedure of Example 81, 1-[3-(4-methoxyphenylthio)propanoyl]-L-proline is obtained.

EXAMPLE 91

1-(3-Methylthiopropanoyl)-L-Pipecolic acid

By substituting L-pipecolic acid for the L-proline in the Procedure A of Example 80, 1-(3-methylthiopropanoyl)-L-pipecolic acid is obtained.

EXAMPLE 92

1-[2-(4-Chlorophenylthio)propanoyl]-L-Proline

By substituting 2-bromopropionyl chloride for the 3-bromopropionyl chloride in the procedure of Example 81, 1-[2-(4-chlorophenylthio)propanoyl]-L-proline is obtained.

EXAMPLE 93

1-[3-[(Diphenylmethyl)thio]-2-benzylpropanoyl)]-L-Proline

Diphenylmethanol (0.92 g) and 1-(3-mercapto-2-benzylpropanoyl)-L-proline (1.5 g) are dissolved in trifluoroacetic acid (10 ml) and the solution is kept at room temperature for 30 minutes. The excess trifluoroacetic acid is removed in vacuo to yield 1-[3-[(diphenylmethyl)thio]-2-benzylpropanoyl]-L-proline.

EXAMPLE 94

1-[4-(4-Chlorophenylthio)butanoyl]-L-Proline

By substituting 4-bromopropionyl chloride for the 3-bromopropionyl chloride in the procedure of Example 81, 1-[4-(4-chlorophenylthio)butanoyl]-L-proline is obtained.

EXAMPLE 95

1-[3-[(Benzylthiomethyl)thio]butanoyl]-L-proline

By substituting 3-mercaptobutanoyl-L-Proline for the 3-mercaptopropanoyl-L-proline in the procedure of Example 82, 1-[3-[(benzylthiomethyl)thio]butanoyl]-L-proline is obtained.

EXAMPLE 96

1-[[4-[(Acetamidomethyl)thio]-2-methylbutanoyl]-L-Proline

By substituting 1-(4-mercapto-2-methylbutanoyl)-L-proline for the 1-(3-mercaptopropanoyl)-L-proline in the procedure of Example 83, 1-[[4-(acetamidomethyl)-thio]-2-methylbutanoyl]-L-proline is obtained.

EXAMPLE 97

1-[3-(Ethyldithio)propanoyl]-L-Proline (A) 3-Mercaptopropanoyl-L-proline (10 g) is added to a solution of ethylthiosulfinate (8.4 g) in methanol (100 ml) and the reaction mixture is stirred vigorously at room temperature for four hours. The methanol is removed in vacuo to yield 1-(3-ethyldithiopropanoyl)-L-proline.

(B) A solution of ethylthiosulfinate (8.4 g) in ethanol (50 ml) is added to an aqueous solution of 3-mercaptopropanoyl-L-proline (10 g) maintained at pH 6–7 by careful addition of sodium hydroxide. The mixture is stirred vigorously at room temperature until negative thiol reaction. The mixture is diluted with water, adjusted to pH 8 and extracted with ethyl acetate, the aqueous phase is acidified to pH 3 and extracted again with ethyl acetate. This latter extract is washed with water, dried and concentrated to dryness to yield 1-[3-(ethyldithio)propanoyl]-L-proline.

EXAMPLE 98

1-[3-[(4-Methylphenyl)dithio]propanoyl]-L-Proline

A solution of 4-methylphenylsulfenyl chloride (1.76 g.) in ether (20 ml) is added to a solution of 3-mercaptopropanoyl-L-proline (2 g) in 0.5 N sodium hydroxide (20 ml) chilled in an ice bath. The mixture is stirred vigorously for one hour, and the aqueous phase is separated, acidified with concentrated hydrochloric acid and extracted with ethyl acetate. The organic phase is washed with water, dried and concentrated to dryness to yield 1-[[3-(4-methylphenyl)dithio]-propanoyl]-L-proline.

EXAMPLE 99

1-[3-(Phenyldithio)propanoyl]-L-Proline

By substituting phenylthiosulfinate [prepared from phenyldisulfide according to U. Weber and P. Hartter, Z. Physiol. Chem., 351, 1384 (1970)] for the ethylthiosulfinate in the procedure of Example 97, 1-[3-(phenyldithio)propanoyl]-L-proline is obtained.

EXAMPLE 100

1-[3-[(2-phenylethyl)dithio]propanoyl]-L-Proline

By substituting 2-phenylethylthiosulfinate (prepared from phenethyldisulfide) for the ethylthiosulfinate in the procedure of Example 97, 1-[3-[(2-phenylethyl)dithio]propanoyl]-L-proline is obtained.

EXAMPLE 101

1-[3-[(2-Hydroxyethyl)dithio]propanoyl]-L-Proline

To a solution of 1,1'-[(sulfinylthio)-bis-(3-propanoyl)]-bis-L-proline (21 g) in methanol (100 ml), mercaptoethanol (4.2 g) is added and the reaction mixture is stirred vigorously at room temperature for four hours. The methanol is removed in vacuo and the residue is purified by chromatography on a silica gel column to yield 1-[3-[(2-hydroxyethyl)dithio]propanoyl]-L-proline.

EXAMPLE 102

1-[2-(Ethyldithio)propanoyl]-L-Proline

By substituting 2-mercaptopropanoyl-L-proline for 3-mercaptopropanoyl-L-proline in the procedure of Example 97, 1-[2-(ethyldithio)propanoyl]-L-proline is obtained.

EXAMPLE 103

1-[3-[(4-Methylphenyl)dithio]butanoyl]-L-Proline

By substituting 3-mercaptobutanoyl-L-proline for the 3-mercaptopropropanoyl-L-proline in the procedure of Example 98, 1-[3-(4-methylphenyl)dithio]butanoyl]-L-proline is obtained.

EXAMPLE 104

1-[3-(Ethyldithio)-2-methylpropanoyl]-L-Proline methyl ester

By substituting 1-(3-mercapto-2-methylpropanoyl)-L-proline for the 3-mercaptopropanoyl-L-proline in the procedure of Example 97 and then treating the product with ethereal diazomethane as in the procedure of Example 72, 1-[3-(ethyldithio)-2-methylpropanoyl]-L-proline methyl ester is obtained.

EXAMPLE 105

1-[3-(Ethyldithio)propanoyl]-L-Azetidine-2-Carboxylic Acid

By substituting 3-mercaptopropanoyl-L-azetidine-2-carboxylic acid for the 3-mercaptopropanoyl-L-proline in the procedure of Example 97, 1-[3-(ethyldithio)-propanoyl]-L-azetidine-2-carboxylic acid is obtained.

EXAMPLE 106

1-[3-[(4-Methylphenyl)dithio]-2-methylpropanoyl]-L-Hydroxyproline

By substituting 1-(3-mercapto-2-methylpropanoyl)-L-hydroxy proline for the 3-mercaptopropanoyl-L-proline in the procedure of Example 98, 1-[3-[(4-methylphenyl)dithio]-2-methylpropanoyl]-L-hydroxyproline is obtained.

EXAMPLE 107

1-[4-(Ethyldithio)butanoyl]-L-Pipecolic acid

By substituting 4-mercaptobutanoyl-L-pipecolic acid for the 3-mercaptopropanoyl-L-proline in the procedure of Example 97, 1-[4-(ethyldithio)butanoyl]-L-pipecolic acid is obtained.

EXAMPLE 108

1-[3-(Ethyldithio)propanoyl]-5-hydroxy-L-Pipecolic acid

By substituting 1-(3-mercaptopropanoyl)-5-hydroxy-L-pipecolic acid for the 3-mercaptopropanoyl-L-proline in the procedure of Example 97, 1-[3-(ethyldithio)-propanoyl]-5-hydroxy-L-pipecolic acid is obtained.

EXAMPLE 109

1-[3-[(2-Amino-2-carboxyethyl)dithio]propanoyl]-L-Proline

A 0.5 M solution of thiocyanogen in glacial acetic acid is prepared by shaking for ten minutes in a sealed flask 600 mg of dry lead thiocyanate with a solution of 75 μl of bromine in 3 ml of acetic acid. After removal of lead bromide and excess lead thiocyanate by centrifugation, 2.5 ml of this solution is mixed with 2.5 ml of a 0.41 M solution of cysteine hydrochloride previously neutralized with dilute sodium hydroxide. This mixture is immediately added to 0.75 ml of a 1.9 M solution of 3-mercaptopropanoyl-L-proline previously neutralized with dilute sodium hydroxide. After twenty minutes the mixture is titrated to incipient brown color with alcoholic iodine, and adjusted to pH 3. The precipitate is removed by filtration and the filtrate is applied to a column of cation exchange resin (Dowex 50). The column is washed with water until no more acidic material is removed and then eluted with pyridine-acetate buffer pH 6.0. The fractions containing the disulfide of cysteine and 3-mercaptopropanoyl-L-proline are pooled and concentrated to dryness.

EXAMPLE 110

1,1'-[Dithiobis(3-propanoyl)]-bis-L-Proline

3-Mercaptopropanoyl-L-proline (0.95 g) is dissolved in water (20 ml) and the pH is adjusted to 6.5 with N-sodium hydroxide. An ethanolic solution of iodine is added dropwise while maintaining the pH at 6.5 with careful addition of N sodium hydroxide. When a permanent yellow color is obtained the addition of iodine is stopped and the color is discharged with a small amount of sodium thiosulfate. The reaction mixture is acidified with concentrated hydrochloric acid and extracted with ethyl acetate. The organic phase is washed with water, dried and concentrated to dryness to yield 1,1'-[dithiobis(3-propanoyl)]-bis-L-proline. The dicyclohexylammonium salt is prepared by addition of dicyclohexylamine to a solution of the free acid in acetonitrile, m.p. 179°–180°.

EXAMPLE 111

1,1'-[Dithiobis(2-D-methyl-3-propanoyl)]-bis-L-Proline

By substituting 3-mercapto-2-D-methylpropanoyl-L-proline for the 3-mercaptopropanoyl-L-proline in the procedure of Example 110, 1,1'-[dithiobis(2-D-methyl-3-propanoyl)]-bis-L-proline is obtained, m.p. 236°–237°.

EXAMPLE 112

1,1'-[Dithiobis(2-propanoyl)-bis-L-Proline

By substituting 2-mercaptopropanoyl-L-proline for the 3-mercaptopropanoyl-L-proline in the procedure of Example 110, 1,1'-[dithiobis(2-propanoyl)]-bis-L-proline is obtained.

EXAMPLE 113

1,1'-(Dithiobisacetyl)-bis-L-hydroxy Proline

By substituting 1-(2-mercaptoacetyl)-L-hydroxyproline for the 3-mercaptopropionyl-L-proline in the procedure of Example 110, 1,1'-(dithiobisacetyl)-bis-L-hydroxyproline is obtained.

EXAMPLE 114

1,1'-(Dithiobisacetyl)-bis-L-Azetidine-2-Carboxylic Acid

By substituting 1-(2-mercaptoacetyl)-L-azetidine-2-carboxylic acid for the 3-mercaptopropanoyl-L-proline in the procedure of Example 110, 1,1'-(dithiobisacetyl)-bis-L-azetidine-2-carboxylic acid is obtained.

EXAMPLE 115

1,1'-[Dithiobis(3-propanoyl)]-bis-L-Pipecolic acid

By substituting 3-mercaptopropanoyl-L-pipecolic acid for the 3-mercaptopropanoyl-L-proline in the procedure of Example 110, 1,1'-[dithiobis(3-propanoyl)]-bis-L-pipecolic acid is obtained.

EXAMPLE 116

1,1'-[Dithiobis(3-propanoyl)]-bis-4-methyl-L-Proline

By substituting 1-(3-mercaptopropanoyl)-4-methyl-L-proline for the 3-mercaptopropanoyl-L-proline in the procedure of Example 110, 1,1'-[dithiobis(3-propanoyl)]-bis-4-methyl-L-proline is obtained.

EXAMPLE 117

1,1'-[Dithiobis(3-propanoyl)]-bis-5-hydroxy-L-Pipecolic acid

By substituting 1-(3-mercaptopropanoyl)-5-hydroxy-L-pipecolic acid for the 3-mercaptopropanoyl-L-proline in the procedure of Example 110, 1,1'-[dithiobis(3-propanoyl)]-bis-5-hydroxy-L-pipecolic acid is obtained.

EXAMPLE 118

1,1'-[Dithiobis(2-benzyl-3-propanoyl)]-bis-L-Proline

By substituting 1-(3-mercapto-2-benzylpropanoyl)-L-proline for the 3-mercaptopropanoyl-L-proline in the procedure of Example 110, 1,1'-[dithiobis(2-benzyl-3-propanoyl)]-bis-L-proline is obtained.

EXAMPLE 119

1,1'-[Dithiobis(2-methyl-3-propanoyl)]-bis-L-Pipecolic acid

By substituting 1-(3-mercapto-2-methylpropanoyl)-L-pipecolic acid for the 3-mercaptopropanoyl-L-proline in the procedure of Example 110, 1,1'-[dithiobis(2-methyl-3-propanoyl)9 -bis-L-pipecolic acid is obtained.

EXAMPLE 120

1,1'-[Dithiobis(4-butanoyl)]-bis-L-Proline

By substituting 4-mercaptobutanoyl-L-proline for the 3-mercaptopropanoyl-L-proline in the procedure of Example 110, 1,1'-[dithiobis(4-butanoyl)]-bis-L-proline is obtained.

EXAMPLE 121

1,1'-[Dithiobis(2-benzyl-4-butanoyl)]-bis-L-Proline

By substituting 1-(4-mercapto-2-benzylbutanoyl)-L-proline for the 3-mercaptopropanoyl-L-proline in the procedure of Example 110, 1,1'-[dithiobis(2-benzyl-4-butanoyl)]-bis-L-proline is obtained.

EXAMPLE 122

1,1'-[Dithiobis(3-butanoyl)]-bis-L-Proline

By substituting 3-mercaptobutanoyl-L-proline for the 3-mercaptopropanoyl-L-proline in the procedure of Example 110, 1,1'-[dithiobis(3-butanoyl)]-bis-L-proline is obtained.

EXAMPLE 123

1,1'-[Dithiobis(3-propanoyl)]-bis-L-Proline methyl ester

A solution of 1,1'-[dithiobis(3-propanoyl)]-bis-L-proline in methanol is treated with ethereal diazomethane until persistent yellow color. After fifteen minutes a few drops of acetic acid are added and the solvents are removed in vacuo to yield, 1,1'-[dithiobis(3-propanoyl)]-bis-L-proline methyl ester.

EXAMPLE 124

1,1'-[Dithiobis(3-propanoyl)]-bis-L-proline amide

A solution of 1,1'-[dithiobis(3-propanoyl)]-bis-L-proline methyl ester in methanol is saturated with ammonia while cooling in an ice-water bath. The reaction mixture is stored for 16 hours at room temperature in a pressure bottle, and then the solvents are removed in vacuo to yield 1,1'-[dithiobis(3-propanoyl)]-bis-L-proline amide.

EXAMPLE 125

1,1'-[Dithiobis[2-phenyl-3-propanoyl)]-bis-L-Proline

By substituting 1-(3-mercapto-2-phenylpropanoyl)-L-proline for the 3-mercaptopropanoyl-L-proline in the procedure of Example 110, 1,1'-[dithiobis(2-phenyl-3-propanoyl)]-bis-L-proline is obtained.

EXAMPLE 126

1,1'-[(Sulfinylthio)-bis-(3-propanoyl)]-bis-L-Proline

While cooling in an ice bath 0.12 mole of peracetic acid is added to a stirred solution of 1,1'-[dithiobis(3-propanoyl)]-bis-L-proline (40 g) in glacial acetic acid (500 ml). The reaction mixture is allowed to stand overnight at room temperature and the solvent is then removed in vacuo to yield 1,1'-[(sulfinylthio)-bis-(3-propanoyl)]-bis-L-proline.

EXAMPLE 127

1,1'-[(Sulfonylthio)-bis-(3-propanoyl)]-bis-L-Proline

A 30% solution of hydrogen peroxide (2.0 ml) is added to a solution of 1,1'-[dithiobis(3-propanoyl)]-bis- L-proline (4 g) in glacial acetic acid (80 ml) and the solution is stored for thirty hours at room temperature. The solvent is removed in vacuo to yield 1,1'-[(sulfonylthio)-bis-(3-propanoyl)]-bis-L-proline.

EXAMPLE 128

1,1'-[(sulfinylthio)-bis-(2-propanoyl)]-bis-L-Proline

By substituting 1,1'-[dithiobis(2-propanoyl)]-bis-L-proline for the 1,1'-[dithiobis(3-propanoyl)]-bis-L-proline in the procedure of Example 126, 1,1'-[(sulfinylthio)-bis-(2-propanoyl)]-bis-L-proline is obtained.

EXAMPLE 129

1,1'-[(Sulfinylthio)-bis-acetyl]-bis-L-Azetidine-2-Carboxylic Acid

By substituting 1,1'-(dithiobisacetyl)-bis-L-azetidine carboxylic acid for the 1,1'-[dithiobis(3-propanoyl)]-bis-L-proline in the procedure of Example 126, 1,1'-[(sulfinylthio)-bis-acetyl]-bis-L-azetidine-2-carboxylic acid is obtained.

EXAMPLE 130

1,1'-[(Sulfinylthio)-bis-(3-propanoyl)]-bis-4-methyl-L-Proline

By substituting 1,1'-[dithiobis(3-propanoyl)]-bis-4-methyl-L-proline for the 1,1'-[dithiobis(3-propanoyl)]-bis-L-proline in the procedure of Example 126, 1,1'-[(sulfinylthio)-bis-(3-propanoyl)]-bis-4-methyl-L-proline is obtained.

EXAMPLE 131

1,1'-[(Sulfinylthio)-bis-(2-benzyl-3-propanoyl)]-bis-L-Proline

By substituting 1,1'-[dithiobis(2-benzyl-3-propanoyl)]-bis-L-proline for the 1,1'-[dithiobis(3-propanoyl)]-bis-L-proline in the procedure of Example 126, 1,1'-[(sulfinylthio)-bis-(2-benzyl-3-propanoyl)]-bis-L-proline is obtained.

EXAMPLE 132

1,1'-[(Sulfinylthio)-bis-(4-butanoyl)]-bis-L-Proline

By substituting 1,1'-[dithiobis(4-butanoyl)]-bis-L-proline for the 1,1'-[dithiobis(3-propanoyl)]-bis-L-proline in the procedure of Example 126, 1,1'-[(sulfinylthio)-bis-(4-butanoyl)]-bis-L-proline is obtained.

EXAMPLE 133

1,1'-[(Sulfinylthio)-bis-(3-butanoyl)]-bis-L-Proline

By substituting 1,1'-[dithiobis(3-butanoyl)]-bis-L-proline for the 1,1'-[dithiobis(3-propanoyl)]-bis-L-proline in the procedure of Example 126, 1,1'-[(sulfinylthio)-bis-(3-butanoyl)]-bis-L-proline is obtained.

EXAMPLE 134

1,1'-[(Sulfinylthio)-bis-(2-methyl-3-propanoyl]-bis-L-Proline

By substituting 1,1'-[dithiobis(2-methyl-3-propanoyl)]-bis-L-proline for the 1,1'-[dithiobis(3-propanoyl)]-bis-L-proline in the procedure of Example 126, 1,1'-[(sulfinylthio)-bis-(2-methyl-3-propanoyl)]-bis-L-proline is obtained.

EXAMPLE 135

1,1'-[(Sulfinylthio)-bis-(2-phenyl-3-propanoyl)]-bis-L-Proline

By substituting 1,1'-[dithiobis(2-phenyl-3-propanoyl)]-bis-L-proline for the 1,1'-[dithiobis(3-propanoyl)]-bis-L-proline in the procedure of Example 126, 1,1'-[(sulfinylthio)-bis-(2-phenyl-3-propanoyl)]-bis-L-proline is obtained.

EXAMPLE 136

1-[3-[[3-(2-Carboxy-1-pyrrolidinyl)-3-oxopropyl]-dithio]-2-methylpropanoyl]-L-Proline By substituting 1,1'-[(sulfinylthio)-bis-(2-methyl-3-propanoyl)]-bis-L-proline for the ethylthiosulfinate in the procedure of Example 97, 1-[3-[[3-(2-carboxy-1-pyrrolidinyl)-3-oxopropyl]dithio]-2-methylpropanoyl]-L-proline is obtained.

EXAMPLE 137

1,1'-[(Sulfonylthio)-bis-acetyl)-bis-L-Hydroxyproline

By substituting 1,1'-(dithiobisacetyl)-bis-L-hydroxy proline for the 1,1'-[dithiobis(3-propanoyl)-bis-L-proline in the procedure of Example 127, 1,1'-[(sulfonylthio)-bis-acetyl]-bis-L-hydroxyproline is obtained.

EXAMPLE 138

1,1'-[(Sulfonylthio)-bis-(3-propanoyl)]-bis-L-Pipecolic acid

By substituting 1,1'-[dithiobis(3-propanoyl)]-bis-L-pipecolic acid for the 1,1'-[dithiobis(3-propanoyl)]-bis-L-proline in the procedure of Example 127, 1,1'-[(sulfonylthio)-bis-(3-propanoyl)]-bis-L-pipecolic acid is obtained.

EXAMPLE 139

1,1'-[(Sulfonylthio)-bis-(3-propanoyl)]-bis-5-hydroxy-L-Pipecolic acid

By substituting 1,1'-[dithiobis(3-propanoyl)]-bis-5-hydroxy-L-pipecolic acid for the 1,1'-[dithiobis-(3-propanoyl)]-bis-L-proline in the procedure of Example 127, 1,1'-[(sulfonylthio)-bis-(3-propanoyl)]-bis-5-hydroxy-L-pipecolic acid is obtained.

EXAMPLE 140

1,1'-[(Sulfonylthio)-bis-(2-methyl-3-propanoyl)]-bis-L-Pipecolic acid

By substituting 1,1'-[dithiobis(2-methyl-3-propanoyl)]-bis-L-pipecolic acid for the 1,1'-[dithiobis(3-propanoyl)]-bis-L-proline in the procedure of Example 127, 1,1'-[(sulfonylthio)-bis-(2-methyl-3-propanoyl)]-bis-L-pipecolic acid is obtained.

EXAMPLE 141

1,1'-[(Sulfonylthio)-bis-(2-benzyl-4-butanoyl)]-bis-L-Proline

By substituting 1,1'-[dithiobis(2-benzyl-4-butanoyl)]-bis-L-proline for the 1,1'-[dithiobis(3-propanoyl)]-bis-L-proline in the procedure of Example 127, 1,1'-[(sulfonylthio)-bis-(2-benzyl-4-butanoyl)]-bis-L-proline is obtained.

EXAMPLE 142

3-Acetylthio-2-phenylpropanoic acid

By substituting 2-phenylacrylic acid for the methacrylic acid in the procedure of Example 25, 3-acetylthio-2-phenylpropanoic acid is obtained.

1-(3-Acetylthio-2-phenylpropanoyl)-L-Proline tert-butyl ester

By substituting 3-acetylthio-2-phenylpropanoic acid for the 3-acetylthio-2-methylpropanoic acid in the procedure of Example 28, 1-(3-acetylthio-2-phenylpropanoyl)-L-proline tert-butyl ester is obtained.

EXAMPLE 143

1-(3-Mercapto-2-phenylpropanoyl)-L-Proline

By substituting 1-(3-acetylthio-2-phenylpropanoyl)-L-proline tert-butyl ester for the 1-(3-acetylthio-2-methylpropanoyl-L-proline tert-butyl ester in the procedure of Example 29, and subjecting the product to ammonolysis as in Example 34, 1-(3-acetylthio-2-phenylpropanoyl)-L-proline and 1-(3-mercapto-2-phenylpropanoyl)-L-proline are obtained.

EXAMPLE 144

1-[3-(Acetylthio)-DL-propanoyl]Pipecolic Acid

Pipecolic acid (6.5 g.) is suspended in 200 ml. of dimethylacetamide. 3-acetylthiopropanoyl chloride (8.3 g.) is added dropwise at 23° to the suspension. A clear solution forms and the temperature rises to 28°. To this clear solution is added N-methylmorpholine (10.1 g.). An immediate precipitate forms and the temperature rises to 34°. The mixture is heated on a steam bath for 1 hour when a clear solution forms. On cooling, the precipitated solid is filtered to yield 5.1 g. of 1-[3-(acetylthio)-DL-propanoyl]pipecolic acid, m.p. 190°–200°. The solvent is removed and the viscous residue is triturated with isopropyl ether to yield 7.8 g. of product, m.p. 98°–101°. Recrystallization from acetone-hexane yields a constant melting solid, m.p. 102°–104°; Rf 0.72 [silica gel, benzene, acetic acid (7:2)].

EXAMPLE 145

DL-1-(3-Mercaptopropanoyl)Pipecolic Acid 12 ml. of concentrated ammonium hydroxide is stirred under nitrogen at 10° for about 15 minutes, then solid 1-[3-(acetylthio)-DL-propanoyl]-pipecolic acid (6.6 g.) is added at 5° to 10°. A clear solution forms after 2–3 minutes. The ice bath is removed and the solution is stirred at room temperature under nitrogen for 45 minutes. The solution is made strongly acid with 20% HCl (cooling) and the precipitated oil is extracted with 3×150 ml. of ethyl acetate. The ethyl acetate extracts are dried over magnesium sulfate and the solvent is removed to yield 6.0 g. of DL-1-(3-mercaptopropanoyl)pipecolic acid, Rf 0.77 [silica gel, benzene, acetic acid (7:1)].

EXAMPLE 146

1-(3-Mercaptopropanoyl)-L-Pipecolic Acid

By substituting L-pipecolic acid for the DL-pipecolic acid in the procedure of Example 144 and then submitting the product to the procedure of Example 145, 1-[3-(acetylthio)propanoyl]-L-pipecolic acid and 1-(3-mercaptopropanoyl)-L-pipecolic acid $R_f$ 0.80 [silica gel, benzene, acetic acid (7:1)], $[\alpha]_D^{20}$ −51.5 (c, 1.0 abs. ethanol), are obtained.

EXAMPLE 147

1-[3-(Acetylthio)-2-methylpropanoyl]-DL-Pipecolic Acid 6.5 g. (0.05 m.) of pipecolic acid are suspended i dimethylacetamide (200 mg.), 9.0 g. (0.05 m.) of 3-acetylthio-2-methylpropanoyl chloride is added dropwise. The temperature rises to 29° and a clear solution forms. Then 10.1 g. of N-methylmorpholine is added all at once and the temperature rises to 34°. The mixture is heated on a steam bath for 1 hour when a clear solution forms. This is allowed to stand at room temperature overnight and the solid which precipitates is filtered to yield 6.1 g., m.p. 203°–204°. The solvent is removed and the viscous residue is triturated with water and 20% HCl. The yellow oil is extracted with 3×150 ml. of ethyl acetate. The ethyl acetate extracts are dried over magnesium sulfate and removed to yield 14 g. of 1-[3-(acetylthio)-2-methylpropanoyl]-DL-pipecolic acid as a viscous oil.

EXAMPLE 148

1-(3-Mercapto-2-methylpropanoyl)-DL-Pipecolic Acid

Aqueous NH$_4$OH (30 ml. water and 20 ml. conc. NH$_4$OH) is stirred under nitrogen at 10° for 15 minutes. This is added to 13.0 g. (0.05 m) off 1-[3-(acetylthio)-2-methylpropanoyl]-DL-pipecolic acid and the resulting solution is stirred for 10 minutes under nitrogen; then at room temperature for 50 minutes. It is then treated with water and 20% HCl and the yellow oil extracted with 3×150 ml. of ethyl acetate. The ethyl acetate extract is dried over magnesium sulfate and removed to yield 11.1 g. 1-(3-mercapto-2-methylpropanoyl)-DL-pipecolic acid as a viscous oil. $R_f$ 0.62 [silica gel, benzene, acetic acid (7:2)].

EXAMPLE 149

3-[(4-Methoxyphenyl)methylthio]-2-methylpropanoic acid p-Methoxy-α-toluene thiol (15.4 g., 0.1 mol.) is added to a solution of methacrylic acid (8.6 g., 0.1 mol.) in 50 ml. 2 N sodium hydroxide. The mixture is heated on the steam bath for three hours, then refluxed for two hours and cooled. The mixture is extracted with ether, then the aqueous layer is acidified with concentrated HCl and extracted with dichloromethane. The acidic extracts are washed with brine, dried (MgSO$_4$) and evaporated in vacuo. The resulting semi-solid is taken up in 50 ml. of dichloromethane, diluted with 50 ml. hexane, and chilled. 3-[(4-methoxyphenyl)methylthio]-2-methylpropanoic acid is collected as a white crystalline solid, m.p. 74°–82° (5.5 g.).

EXAMPLE 150

1-[3-(4-Methoxyphenyl)methylthio]-2-methylpropanoyl-L-Proline tert-butyl ester 3-[(4-methoxyphenyl)methylthio]-2-methylpropanoic acid (3.6 g., 0.015 mol.), L-proline tert-butyl ester (2.6 g., 0.015 mol.), and dicyclohexylcarbodiimide (3.1 g., 0.015 mol.) are dissolved in 50 ml. of dichloromethane and stirred thirty minutes at 0°. The cooling bath is removed and the mixture stirred overnight (sixteen hours). The resulting suspension is filtered and the filtrate washed with 5% potassium bisulfate, saturated sodium bicarbonate and brine, then dried (MgSO₄) and evaporated in vacuo. The resulting clear oil is applied to a 250 ml. silica gel column and chromatographed using 20% ethyl acetate/hexane as eluant. The main fraction ($R_f$=0.70, silica gel, ethyl acetate) is evaporated to 5.5 g. (93%) of 1-[3-(4-methoxyphenyl)methylthio]-2-methylpropanoyl-L-proline tert-butyl ester as a clear oil. $R_f$=0.70 (silica gel, ethyl acetate); $R_f$=0.60 (silica gel, ether).

EXAMPLE 151

1-(3-Mercapto-2-methylpropanoyl)-L-Proline

The ester from Example 150 (1.2 g., 0.003 mol.), anisole (5 ml.) and trifluoromethanesulfonic acid (0.5 ml.) are dissolved in 20 ml. of trifluoroacetic acid under nitrogen, and the resulting red solution let stand one hour at room temperature. The solution is evaporated in vacuo to a red residue which is taken up in ethyl acetate and washed with water, brine, then dried (MgSO₄) and evaporated. The residue is repeatedly triturated with hexane and the residual hexane evaporated; the oil residue amounts to 0.4 g. A portion (180 mg.) of this material is subjected to preparative thin-layer chromatography on 2 mm silica gel plates using benzene/acetic acid 75:25 as eluant. The main nitroprusside-positive band ($R_f$=0.40) is recovered, affording 135 mg. of 1-(3-mercapto-2-methylpropanoyl)-L-proline as an oil. TLC using benzene/acetic acid 75:25 ($R_f$=0.40) and chloroform/methanol/acetic acid 50:40:10 ($R_f$=0.62).

EXAMPLE 152

1-(3-Mercapto-2-D-methylpropanoyl)-L-Proline

Under a blanket of argon 1-[3-(acetylthio)-2-D-methylpropanoyl]-L-proline (10.0 g.) is slurried in water (150 ml.) at 10°. To this mixture is added 5 N sodium hydroxide and the pH of the solution maintained at 13 for 1.5 hours. After this time, when the uptake of sodium hydroxide had ceased, the solution is acidified to a pH=2.0 with concentrated sulfuric acid.

The aqueous solution is then extracted three times with methylene chloride (3×150 ml.) and the combined methylene chloride fractions concentrated to an oil. The concentrate is taken up in ethyl acetate, filtered and the filtrate diluted with hexane (30 ml.). An additional amount of hexane is added after ½ hour and then the mixture cooled to 10° for 1 hour.

The crystals are filtered and washed with hexane (2×25 ml.) and dried to constant weight to give 1-(3-mercapto-2-D-methylpropanoyl)-L-proline as white crystals, 6.26 g., m.p. 100°-102°.

EXAMPLE 153

1-[3-Tosyloxy-2-methylpropanoyl]-L-Proline

By substituting 3-tosyloxy-2-methylpropanoic acid chloride for the 3-acetylthio-2-methylpropanoic acid chloride in the procedure of Example 29b 1-[3-tosyloxy-2-methylpropanoyl]-L-proline is obtained.

EXAMPLE 154

1-[3-Acetylthio-2-methylpropanoyl]-L-Proline

1-[3-Tosyloxy-2-methylpropanoyl]-L-proline (3.5 g.) is added to a solution of thioacetic acid (1.14 g.), and triethylamine (3.5 ml.) in ethyl acetate (20 ml.). The solution is maintained at 50° for three hours, cooled, diluted with ethyl acetate (100 ml.), and washed with dilute hydrochloric acid. The organic layer is dried and concentrated to dryness in vacuo. The residue is dissolved in acetonitrile and dicyclohexylamine is added. The crystalline precipitate is recrystallized from isopropanol to yield 1-[3-acetylthio-2-D-methylpropanoyl)-L-proline, dicyclohexylamine salt, m.p. 187°-188°, $[\alpha]_D^{25}$ −67° (c 1,4, EtOH). This salt is converted to the free acid, m.p. 83°-85° (an isomorphic form of m.p. 104°-105° is obtained if the crystallizing solution is seeded with high melting material).

EXAMPLE 155

1-(3-Mercaptopropanoyl)-L-Proline, t-butyl ester

To a stirred solution of 1.71 g. (10 mmoles) of proline t-butyl ester and 1.35 g. (10 mmoles) of 1-hydroxybenzotriazole hydrate in 20 ml. of N,N-dimethylformamide at 0°-5° are added 2.06 g. (10 mmole) of N,N'-dicyclohexylcarbodiimide. The mixture is stirred for 10 minutes, followed by the addition of 1.06 g. (10 mmole) of 3-mercaptopropanoic acid in 2 ml. of N,N-dimethylformamide. The mixture is then stirred at 0°-5° for 1 hour, and at room temperature overnight.

The precipitated N,N'-dicyclohexylurea is filtered off, and the filtrate concentrated in vacuo. The residue is taken up in ethyl acetate, washed thoroughly with saturated aqueous sodium bicarbonate, dried, and concentrated in vacuo to 2.5 g. of oil.

The oil is taken up in 1:1 ethyl acetate-hexane and applied to a silica gel column (100 g.). Elution with 1:1 ethyl acetate-hexane affords 1.40 g. (54%) of 1-(3-mercaptopropanoyl)-L-proline, t-butyl ester as an oil, which crystallizes on standing. Recrystallization from ether-hexane yields 0.9 g. of colorless crystalline solid, m.p. 55°-60°, identical to the compound of Example 17.

EXAMPLE 156

1-(3-Mercaptopropanoyl)-L-Proline

A solution of 75 mg. (0.27 mmole) of 1-[3-[[(ethylamino)carbonyl]thio]propanoyl]-L-proline in 1 ml. each of concentrated ammonium hydroxide and water is allowed to stand at room temperature for 18 hours under argon. The solution is diluted with a small amount of water and extracted with ether. The aqueous layer is acidified with cold concentrated hydrochloric acid and extracted with ethyl acetate. The combined extracts are dried and concentrated in vacuo to give a compound identical with the product of Example 18. TLC (silica gel; benzene:acetic acid 7:3) $R_f$ 0.4.

EXAMPLE 157

Methacryloyl-L-Proline

L-proline (23.0 g., 0.2 mol.) is dissolved in 100 ml. water and stirred in an ice bath. Methacryloyl chloride (19.6 ml., 0.2 mol.) in 25 ml. of methyl isobutyl ketone is added dropwise over three hours. Sodium hydroxide solution (2 N) is added simultaneously, maintaining the pH of the reaction mixture at 7.0. Addition of base is continued for four hours after addition of acid chloride has been completed. The reaction mixture is adjusted to pH 5 with concentrated HCl and extracted with ethyl acetate. The aqueous layer is then acidified to pH 2.5 and extracted thoroughly with ethyl acetate. The acidic extracts are washed with brine and dried (MgSO₄). The ethyl acetate solution is treated with dicyclohexylamine (40 ml.) and chilled overnight. The resulting white precipitate is filtered and dried, yielding 29 g. (39%) of white solid, m.p. 202°-210°. The solid is crystallized from 1.5 liters 3:1 acetonitrile/isopropanol to yield 19.7 g. of methacryloyl-L-proline, dicyclohexylamine salt as fine white needles, m.p. 202°–210°.

The salt is dissolved in water/ethyl acetate and the mixture acidified with concentrated HCl. The resulting suspension is filtered to remove a fine white precipitate which is washed well with ethyl acetate. The filtrate is saturated with sodium chloride and extracted thoroughly with ethyl acetate. The extracts are washed with brine, dried (MgSO$_4$) and evaporated to a clear oil which solidifies. Crystallization from ethyl acetate/hexane yields 7.5 g. (83%) of methacryloyl-L-proline as a white crystalline solid, m.p. 89°–93°. An analytical sample is obtained by recrystallization, m.p. 95°–98°.

EXAMPLE 158

1-(3-Acetylthio-2-D-methylpropanoyl)-L-proline

Methacryloyl-L-proline (183 mg., 0.001 mol.) is dissolved in thiolacetic acid (0.5 ml.) and allowed to stand at room temperature for sixteen hours. The solution is evaporated in vacuo to a yellow residue. Preparative thin layer chromatography (silica gel, dichloromethane/methanol/acetic acid 90:5:5) allows isolation of a clear oil (240 mg.) as the main fraction. TLC (dichloromethane/methanol/acetic acid 90:5:5) shows this material to be 1-(3-acetylthio-2-DL-methylpropanoyl)-L-proline corresponding to the product of Example 29B. $R_f$=0.35; (benzene/acetic acid 75:25) $R_f$=0.38.

The oil is dissolved in 3 ml. acetonitrile, treated with dicyclohexylamine until the solution is basic, and chilled. A white crystalline solid (106 mg.) m.p. 175°–181°, is collected. Crystallization from isopropanol gives 1-(3-acetylthio-2-D-methylpropanoyl)-L-proline, dicyclohexylamine salt, m.p. 187°–188°, identical with this product in Example 29A.

EXAMPLE 159

1-[Dithiobis-(2-methyl-3-propanoyl)]-bis-L-Proline

By substituting 3,3'-dithiobis-2-methylpropanoic acid for the 3-acetylthio-2-methylpropanoic acid in the procedure of Example 29B, 1-[dithiobis-(2-methyl-3-propanoyl)]-bis-L-proline is obtained.

EXAMPLE 160

1-(3-Mercapto-2-methylpropanoyl)-L-Proline

Zinc dust (10.0 g.) is added to a slurry of the product of Example 159 (5.0 g.) in 100 ml. of 1.0 N sulfuric acid and the mixture is stirred at 18° for four hours under a blanket of nitrogen. The solution is then filtered, the zinc washed with water (20 ml.) and the combined filtrates are extracted with methylene chloride (3×75 ml.). The methylene chloride washes are back extracted with water (25 ml.) and then the organic solution concentrated to an oil. This oil is taken up in ethyl acetate (20 ml.) and filtered. Hexane (15 ml.) is added to the filtrate and the mixture is stirred for 15 minutes. After this time, an additional volume of hexane (30 ml.) is added and the solution cooled to 5° for 1 hour. The mixture is then filtered, and the product is washed with hexane (2×10 ml.) and dried to give 4.17 g. of white crystals of the product, 1-(3-mercapto-2-methylpropanoyl)-L-proline. TLC, $R_f$=0.60 (Solvent system: benzene/acetic acid 75:25).

EXAMPLE 161

3-Benzylthio-2-methylpropanoic acid

By substituting α-toluenethiol for p-methoxy-α-toluenethiol in the procedure of Example 149, 3-benzylthio-2-methylpropanoic acid is obtained.

EXAMPLE 162

1-[3-(Benzylthio)-2-methylpropanoyl]-L-Proline tert.butyl ester

By substituting 3-benzylthio-2-methylpropanoic acid for the 3-[(4-methoxyphenyl)methylthio]-2-methylpropanoic acid in the procedure of Example 150, 1-[3-(benzylthio)-2-methylpropanoyl]-L-proline tert.butyl ester is obtained.

EXAMPLE 163

1-[3-(Benzylthio)-2-methylpropanoyl]-L-Proline

1-[3-(benzylthio)-2-methylpropanoyl]-L-proline tert.butyl ester (7.8 g.) is dissolved in a mixture of anisole (55 ml.) and trifluoroacetic acid (110 ml.). After one hour storage at room temperature, the solvent is removed in vacuo and the residue is dissolved in ether, washed several times with saturated sodium chloride, dried over magnesium sulfate and evaporated to dryness in vacuo to yield 1-[3-(benzylthio)-2-methylpropanoyl]-L-proline. $R_f$ 0.5 (Silica gel, Benzene/acetic acid 3:1) $R_f$ 0.5. (Silica gel, Methyl-ethylketone/acetic acid/pyridine/water 14:1:2:1).

EXAMPLE 164

1-(3-Mercapto-2-methylpropanoyl)-L-Proline

1-[3-(benzylthio)-2-methylpropanoyl]-L-proline (0.1 g.) is suspended in boiling liquid ammonia (10 ml.) and small pieces of sodium are added with stirring until persistent blue color. The color is discharged with a few crystals of ammonium sulfate and the ammonia is allowed to evaporate under a current of nitrogen. The residue is dissolved in a mixture of dilute hydrochloric acid and ethyl acetate. The organic layer is dried and concentrated to dryness in vacuo to yield 1-(3-mercapto-2-methylpropanoyl)-L-proline. $R_f$ 0.35 (Silica gel; Benzene/acetic acid 3:1), $R_f$ 0.5 (Silica gel; Methyl-ethylketone/acetic acid/pyridine/water 14:1:2:1) identical to the compound of Example 34.

EXAMPLE 165

3-Triphenylmethylthio-2-methylpropanoic acid

A solution of 3-mercapto-2-methylpropanoic acid (1.2 g.) and tritylchloride (2.9 g.) in methylene chloride (50 ml.) is kept at room temperature for 2 hours. The mixture is warmed in a steam bath for 20 minutes and then evaporated to dryness in vacuo and the residue is dissolved in saturated aqueous sodium bicarbonate and the solution is washed with ethyl acetate. The aqueous phase is acidified to pH 3 and extracted with ethyl acetate. The organic layer is dried and concentrated to dryness to give 3-triphenylmethylthio-2-methylpropanoic acid. $R_f$ 0.8 (Silica gel, Benzene/acetic acid 3:1).

EXAMPLE 166

1-[3-(Triphenylmethylthio)-2-methylpropanoyl]-L-Proline tert.butyl ester

By substituting 3-triphenylmethylthio-2-methylpropanoic acid for the 3-[(4-methoxyphenyl)methylthio]-2-methylpropanoic acid in the procedure of Example 150, 1-[3-(triphenylmethylthio)-2-methylpropanoyl]-L-proline tert.butyl ester is obtained.

EXAMPLE 167

1-[3-(Triphenylmethylthio)-2-methylpropanoyl]-L-Proline

3-Triphenylmethylthio-2-methylpropanoic acid (1.8 g.) and N,N'-carbonyldiimidazole (0.8 g.) are dissolved in tetrahydrofuran (10 ml.) with stirring at room temperature. After twenty minutes, the solution is added to a mixture of L-proline (0.6 g.) and N-methylmorpholine (1 g.) in dimethylacetamide (20 ml.). The resulting mixture is stirred overnight at room temperature, concentrated to dryness and the residue dissolved in a mixture of ethyl acetate and 10% aqueous potassium bisulfate. The organic layer is separated and dried and concentrated to dryness in vacuo to obtain 1-[3-(triphenylmethylthio)-2-methylpropanoyl]-L-proline. $R_f = 0.4$ (Silica gel, Benzene/acetic acid 3:1), $R_f$ 1.0 (Silica gel, Methyl-ethylketone/acetic acid/pyridine/water 14:1:2:1).

EXAMPLE 168

1-[3-Mercapto-2-methylpropanoyl]-L-Proline

1-[3-(triphenylmethylthio)-2-methylpropanoyl]-L-proline tert.butyl ester (5 g.) is dissolved in a mixture of anisole (55 ml.) and trifluoroacetic acid (110 ml.). After one hour storage at room temperature, the solvents are removed in vacuo and the residue is applied to a column of silica gel equilibrated with benzene:acetic acid (75:25) and eluted with the same solvent. The fractions corresponding to the component with $R_f$ 0.40 (TLC silica gel with same system) are pooled and concentrated to dryness to yield 1-[3-mercapto-2-methylpropanoyl]-L-proline. $R_f$ 0.62 (silica gel, chloroform/methanol:acetic acid:water 50:40:10), identical to the compound of Example 34.

EXAMPLE 169

3-(Tetrahydropyran-2-ylthio)-2-methylpropanoic acid

To a solution of 3-mercapto-2-methylpropanoic acid (2.4 g.) and freshly distilled 2,3-dihydro-4H-pyrane (1.9 g.) in benzene (60 ml.), boron trifluoride etherate (2.8 g.) is added. After two hours, potassium carbonate (4 g.) is added, the mixture is stirred and filtered. The filtrate is concentrated to dryness to yield 3-(tetrahydropyran-2-ylthio)-2-methylpropanoic acid.

EXAMPLE 170

1-[3-(Tetrahydropyran-2-ylthio)-2-methylpropanoyl]-L-Proline

By substituting 3-(tetrahydropyran-2-ylthio)-2-methylpropanoic acid for the 3-triphenylmethylthio-2-methylpropanoic acid in the procedure of Example 167, 1-[3-(tetrahydropyran-2-ylthio)-2-methylpropanoyl]-L-proline is obtained. $R_f$ 0.8 (Silica gel, Benzene/acetic acid 3:1; $R_f$ 0.75 (Silica gel, Methyl-ethylketone/Acetic acid/pyridine/water; 14:1:2:1).

EXAMPLE 171

1-(3-Mercapto-2-methylpropanoyl)-L-Proline

A solution of 1-[3-(tetrahydropyran-2-ylthio)-2-methylpropanoyl]-L-proline (1 g.) in a mixture of methanol (25 ml.) and concentrated hydrochloric acid (25 ml.) is stored at room temperature for 30 minutes. The solvents are removed in vacuo to yield 1-(3-mercapto-2-methylpropanoyl)-L-proline. $R_f$ 0.35 (silica gel, Benzene/acetic acid, 3:1), $R_f$ 0.5 (silica gel, Methyl-ethylketone/acetic acid/pyridine/water (14:1:2:1) identical to the compound of Example 34.

EXAMPLE 172

3-Acetamidomethylthio-2-methylpropanoic acid

3-Mercapto-2-methylpropanoic acid (2.4 g.) and N-hydroxymethylacetamide (1.8 g.) are dissolved in trifluoroacetic acid and the solution is stored at room temperature for one hour. The trifluoroacetic acid is removed in vacuo and the residue is dried in vacuo over potassium hydroxide to yield 3-acetamidomethylthio-2-methylpropanoic acid.

EXAMPLE 173

1-[3-(Acetamidomethylthio)-2-methylpropanoyl]-L-Proline

By substituting 3-acetamidomethylthio-2-methylpropanoic acid for the 3-(tetrahydropyran-2-yl thio)-2-methylpropanoic acid in the procedure of Example 170 1-[3-(acetamidomethylthio)-2-methylpropanoyl]-L-proline is obtained. $R_f$ 0.2 (Silica gel, Benzene/acetic acid 3:1) $R_f$ 0.3 (Silica gel, Methyl-ethylketone/acetic acid/pyridine/water 14:1:2:1).

EXAMPLE 174

1-(3-Mercapto-2-methylpropanoyl)-L-Proline

1-[3-(acetamidomethylthio)-2-methylpropanoyl]-L-proline (1.4 g.) and mercuric acetate (1.93 g.) are dissolved in a mixture of acetic acid (25 ml.) and water (25 ml.). After one hour stirring on the steam bath, hydrogen sulfide is bubbled through until no more precipitation of mercuric sulfide is observed. The mixture is filtered, the precipitate is washed with ethanol, and the filtrate is concentrated to dryness in vacuo to yield 1-(3-mercapto-2-methylpropanoyl)-L-proline. $R_f$ 0.35 (Silica gel, Benzene/Acetic acid 3:1); $R_f$ 0.5 (Silica gel, Methyl-ethylketone/Acetic acid/pyridine/water 14:1:2:1) identical to the compound of Example 34.

EXAMPLE 175

1-(3-Mercapto-2-methylpropanoyl)-L-Proline tert.butyl ester

To the cold (5°) solution of 1.2 g. (10 mMol.) of 3-mercapto-2-methylpropanoic acid and 1.7 g. (10 mMol.) of L-proline tert.butyl ester in 25 ml. dichloromethane 2.26 g. of dicyclohexylcarbodiimide in 5 ml. dichloromethane is added in portions. After 2 hours at room temperature, 5 drops of acetic acid are added, the mixture is filtered and the filtrate evaporated to an oily residue. This residue is taken up in 20 ml. of petroleum ether-ethyl acetate (3:1) and applied to a 150 ml. silica gel column prepared in petroleum ether. The fraction eluted with petroleum ether-ethyl acetate (1:1) contains the product, 1-(3-Mercapto-2-methylpropanoyl)-L-proline tert.butyl ester. This fraction (0.6 g.) is dried over $P_2O_5$ in vacuo for 12 hours. $R_f$ 0.6 (Silica gel, Benzene/Acetic acid 3:1), $R_f$ 0.8 (Silica gel, Methyl-ethylketone/acetic acid/pyridine/water 14:1:2:1).

EXAMPLE 176

1-(3-Mercapto-2-methylpropanoyl)-L-Proline

By substituting 1-(3-mercapto-2-methylpropanoyl)-L-proline tert.butyl ester for the 1-(3-mercaptopropanoyl-L-proline tert.butyl ester in the procedure of Example 18C, 1-(3-mercapto-2-methylpropanoyl)-L-proline is obtained. $R_f$ 0.35 (Silica gel, Benzene/acetic acid 3:1), $R_f$ 0.5 (Silica gel, Methyl-ethylketone/Acetic acid/Pyridine/Water 14:1:2:1), identical to the compound of Example 34.

The racemic form of the final product in any of the foregoing examples is produced by utilizing the DL-form of the starting amino acid instead of the L-form.

Similarly, the D-form of the final products in any of the foregoing examples is produced by utilizing the D-form of the starting amino acid instead of the L-form.

EXAMPLE 177

1000 tablets each containing 100 mg. of 1-(2-mercaptopropanoyl)-L-proline are produced from the following ingredients:

| 1-(2-Mercaptopropanoyl)-L-proline | 100 g. |
|---|---|
| Corn starch | 50 g. |
| Gelatin | 7.5 g. |
| Avicel (microcrystalline cellulose) | 25 g. |
| Magnesium stearate | 2.5 g. |

The 1-(2-mercaptopropanoyl)-L-proline and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg. of active ingredient.

EXAMPLE 178

By substituting 100 g. of 1-(3-mercapto-2-D-methylpropanoyl)-L-proline for the 1-(2-mercaptopropanoyl)-L-proline in Example 177, 1000 tablets each containing 100 mg. of the 1-(3-mercapto-2-D-methylpropanoyl-L-proline are produced.

EXAMPLE 179

1000 tablets each containing 200 mg. of 1-(2-mercaptoacetyl)-L-proline are produced from the following ingredients:

| 1-(2-Mercaptoacetyl)-L-proline | 200 g. |
|---|---|
| Lactose | 100 g. |
| Avicel | 150 g. |
| Corn starch | 50 g. |
| Magnesium stearate | 5 g. |

The 1-(2-mercaptoacetyl)-L-proline, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow #6.

EXAMPLE 180

Two piece #1 gelatin capsules each containing 250 mg. of 1-(2-mercaptopropanoyl)-L-proline are filled with a mixture of the following ingredients:

| 1-(2-Mercaptopropanoyl)-L-proline | 250 mg. |
|---|---|
| Magnesium stearate | 7 mg. |
| USP lactose | 193 mg. |

EXAMPLE 181

An injectable solution is produced as follows:

| 1-(2-Mercaptopropanoyl)-L-proline | 500 mg. |
|---|---|
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

EXAMPLE 182

By substituting 100 g. of 1,1'-[dithiobis(2-D-methyl-3-propanoyl)]-bis-L-proline for the 1-(2-mercaptopropanoyl)-L-proline in Example 177, 1000 tablets each containing 100 mg. of the 1,1'-[dithiobis[2-D-methyl-3-propanoyl)]-bis-L-proline are produced.

Each of the products of the examples can be similarly formulated by substituting it for the active ingredient in Examples 177, 179, 180 or 181.

What is claimed is:

1. A compound of the formula

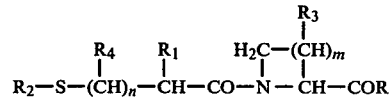

wherein R is hydroxy, $NH_2$ or lower alkoxy;

$R_1$ and $R_4$ each is hydrogen, lower alkyl, phenyl or phenyl-lower alkyl;

$R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoylamidomethyl,

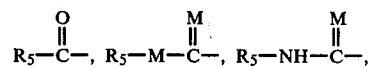

$R_6$—S— or $R_7$;

$R_3$ is hydrogen, hydroxy or lower alkyl;

$R_5$ is lower alkyl, phenyl or phenyl-lower alkyl;

$R_6$ is lower alkyl, phenyl, substituted phenyl, wherein the phenyl substituent is halo, lower alkyl or lower alkoxy, hydroxy-lower alkyl or amino(carboxy)-lower alkyl;

$R_7$ is

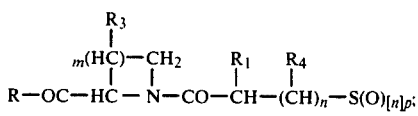

M is O or S;

m is 3;

n and p each is 0, 1 or 2; and basic salts thereof, said lower alkoxy, lower alkyl and lower alkanoyl groups having up to seven carbon atoms.

2. A compound as in claim 1 wherein R is hydroxy or lower alkoxy; $R_1$ is hydrogen or lower alkyl; $R_2$ is hydrogen, $R_5$—CO, $R_6$—S—, or $R_7$; $R_3$ and $R_4$ each is hydrogen; $R_5$ is lower alkyl or phenyl; $R_6$ is lower alkyl; $R_7$ is

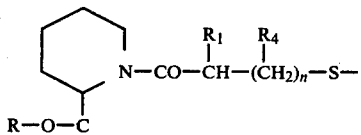

wherein R, $R_1$ and $R_4$ have the same meaning as above; n is 0, 1 or 2; and p is 0.

3. A compound as in claim 1 wherein $R_3$ and $R_4$ each is hydrogen.

4. A compound as in claim 1 wherein $R_3$ is hydrogen.

5. A compound of the formula

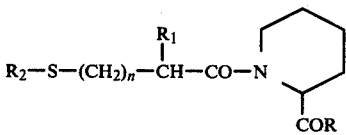

wherein R is hydroxy or lower alkoxy;

$R_1$ is hydrogen or lower alkyl;

$R_2$ is hydrogen or lower alkanoyl;

n is 0, 1 or 2; and physiologically acceptable salts thereof, said lower alkoxy, lower alkyl and lower alkanoyl groups having up to seven carbon atoms.

6. A compound as in claim 5 wherein R is hydroxy.

7. A compound as in claim 5 wherein n is 1.

8. A compound as in claim 5 wherein $R_2$ is hydrogen or lower alkanoyl.

9. A compound as in claim 5 wherein $R_2$ is hydrogen.

10. A compound as in claim 5 wherein $R_2$ is acetyl.

11. A compound as in claim 5 wherein $R_1$ is hydrogen or lower alkyl.

12. A compound as in claim 5 wherein $R_1$ is hydrogen or methyl.

13. A compound as in claim 5 wherein R is hydroxy and $R_1$ is hydrogen or methyl.

14. A compound as in claim 5 wherein R is hydroxy, $R_1$ is hydrogen or methyl, $R_2$ is hydrogen or acetyl and n is 0, 1 or 2.

15. A compound as in claim 5 wherein R is hydroxy, $R_1$ and $R_2$ each is hydrogen and n is 0.

16. A compound as in claim 5 wherein R is hydroxy, $R_1$ is hydrogen, $R_2$ is acetyl and n is 1.

17. A compound as in claim 5 wherein R is hydroxy, $R_1$ and $R_2$ each is hydrogen and n is 1.

18. A compound as in claim 5 wherein R is hydroxy, $R_1$ is methyl, $R_2$ is hydrogen and n is 1.

19. The L-form of a compound of claim 5.

20. The compound of claim 18 in which the piperidine is in the L-form.

21. A compound as in claim 5 wherein R is hydroxy, $R_1$ is hydrogen, $R_2$ is lower alkylthio and n is 2.

22. A compound as in claim 1 wherein $R_2$ is

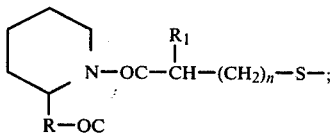

each R is hydroxy; each $R_1$ is hydrogen or lower alkyl; and each n is 0 to 2.

23. A compound as in claim 22 wherein each R is hydroxy; each $R_1$ is methyl and each n is 1.

24. The compound according to claim 1 having the name 1-(3-mercapto-2-methylpropanoyl)-L-pipecolic acid.

25. The compound according to claim 1 having the name 1,1'-[dithiobis(2-methyl-3-propanoyl)]-bis-L-pipecolic acid.

26. The compound of claim 17 in which the piperidine is in the L-form.

27. A composition for reducing blood pressure comprising about 10 to 500 mg. of a compound of claim 1 and a pharmaceutically acceptable vehicle therefor.

28. A composition for reducing blood pressure comprising about 10 to 500 mg. of a compound of claim 18 and a pharmaceutically acceptable vehicle therefor.

29. A composition for reducing blood pressure comprising about 10 to 500 mg. of a compound of claim 17 and a pharmaceutically acceptable vehicle therefor.

30. A composition for reducing blood pressure comprising about 10 to 500 mg. of the compound of claim 24 and a pharmaceutically acceptable vehicle therefor.

31. A composition for reducing blood pressure comprising about 10 to 500 mg. of the compound of claim 25 and a pharmaceutically acceptable vehicle therefor.

32. A method for reducing blood pressure in a hypertensive mammal which comprises administering to said mammal an effective hypotensive amount of a composition comprisng a compound having the formula in claim 1, or a physiologically acceptable salt thereof, and a pharmaceutically acceptable vehicle therefor.

33. A method for reducing blood pressure in a hypertensive mammal which comprises administering to said mammal an effective hypotensive amount of a composition comprising a compound of claim 18 and a pharmaceutically acceptable vehicle therefor.

34. A method for reducing blood pressure in a hypertensive mammal which comprises administering to said mammal an effective hypotensive amount of a composition comprising a compound of claim 17 and a pharmaceutically acceptable vehicle therefor.

35. A method for reducing blood pressure in a hypertensive mammal which comprises administering to said mammal an effective hypotensive amount of a composition comprising the compound of claim 24 and a pharmaceutically acceptable vehicle therefor.

36. A method for reducing blood pressure in a hypertensive mammal which comprises administering to said mammal an effective hypotensive amount of a composition comprising the compound of claim 25 and a pharmaceutically acceptable vehicle therefor.

* * * * *

UNITED STATES PATENT AND TRADEMARK OFFICE
CERTIFICATE OF CORRECTION

PATENT NO. : 4,154,840
DATED : May 15, 1979
INVENTOR(S) : Miguel A. Ondetti et al.

It is certified that error appears in the above-identified patent and that said Letters Patent are hereby corrected as shown below:

Col. 22, line 6, "Ether" should read -- Ethyl --.
Col. 23, line 21, "3-[[methylamino)" should read -- 3-[[(methylamino) --.
Col. 32, line 2, "propanoyl)9-" should read -- propanoyl)] --.
Col. 36, line 8, "i" should read -- in --.
Col. 46, lines 22-24, should read --- 25. The compound according to claim 1 having the name 1,1'-bis-L- pipecolic acid ---.

Signed and Sealed this

Twenty-third Day of September 1980

[SEAL]

Attest:

SIDNEY A. DIAMOND

Attesting Officer

Commissioner of Patents and Trademarks